US009961899B2

(12) United States Patent
Ding et al.

(10) Patent No.: US 9,961,899 B2
(45) Date of Patent: *May 8, 2018

(54) NEMATICIDAL AQUEOUS SUSPENSION CONCENTRATE COMPOSITIONS

(71) Applicant: Monsanto Technology LLC, St. Louis, MO (US)

(72) Inventors: Yiwei Ding, Ballwin, MO (US); Shaun Raj Selness, Chesterfield, MO (US); Urszula J. Slomczynska, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 32 days.

This patent is subject to a terminal disclaimer.

(21) Appl. No.: 14/649,438

(22) PCT Filed: Dec. 4, 2013

(86) PCT No.: PCT/US2013/073128
§ 371 (c)(1),
(2) Date: Jun. 3, 2015

(87) PCT Pub. No.: WO2014/089219
PCT Pub. Date: Jun. 12, 2014

(65) Prior Publication Data
US 2015/0342189 A1  Dec. 3, 2015

Related U.S. Application Data

(60) Provisional application No. 61/733,239, filed on Dec. 4, 2012.

(51) Int. Cl.
| *A01N 43/82* | (2006.01) |
| *A01N 37/42* | (2006.01) |
| *A01N 25/02* | (2006.01) |
| *A01N 37/36* | (2006.01) |
| *A01N 43/50* | (2006.01) |
| *A01N 25/04* | (2006.01) |
| *A01N 43/56* | (2006.01) |
| *A01N 43/653* | (2006.01) |

(52) U.S. Cl.
CPC ............ *A01N 43/82* (2013.01); *A01N 25/02* (2013.01); *A01N 25/04* (2013.01); *A01N 37/36* (2013.01); *A01N 37/42* (2013.01); *A01N 43/50* (2013.01); *A01N 43/56* (2013.01); *A01N 43/653* (2013.01)

(58) Field of Classification Search
None
See application file for complete search history.

(56) References Cited

U.S. PATENT DOCUMENTS

| 3,770,754 | A | 11/1973 | Parsons |
| 4,465,017 | A | 8/1984 | Simmons |
| 4,759,945 | A | 7/1988 | Nemecek et al. |
| 4,871,753 | A | 10/1989 | Rohr |
| 5,080,925 | A | 1/1992 | Kouno |
| 5,107,787 | A | 4/1992 | Kouno |
| 5,389,399 | A | 2/1995 | Bazin et al. |
| 5,554,445 | A | 9/1996 | Struszczyk et al. |
| 5,891,246 | A | 4/1999 | Lund |
| 5,918,413 | A | 7/1999 | Otani et al. |
| 6,001,829 | A | 12/1999 | Krämer et al. |
| 6,939,831 | B1 | 9/2005 | Caminade et al. |
| 8,063,041 | B2 | 11/2011 | Andreella et al. |
| 8,163,930 | B2 | 4/2012 | Cohen et al. |
| 2002/0132813 | A1 | 9/2002 | Schaper et al. |
| 2004/0127521 | A1 | 7/2004 | Cai et al. |
| 2006/0166898 | A1* | 7/2006 | Chen .................... A01N 25/04 514/22 |
| 2009/0048311 | A1* | 2/2009 | Williams ............... A01N 43/76 514/364 |
| 2009/0054234 | A1 | 2/2009 | Long |
| 2010/0210849 | A1 | 8/2010 | Slomczynska et al. |
| 2011/0028320 | A1 | 2/2011 | Slomczynska et al. |
| 2011/0257010 | A1* | 10/2011 | Koltzenburg .......... A01N 25/04 504/100 |
| 2012/0157314 | A1 | 6/2012 | Ahrens et al. |

(Continued)

FOREIGN PATENT DOCUMENTS

| EP | 1 790 229 A1 | 5/2007 |
| JP | S47-27025 B | 7/1972 |
| WO | 2005/089545 A1 | 9/2005 |

(Continued)

OTHER PUBLICATIONS

Dyno-Mill website.*
Liu, B., "Pesticide Formulation Processing Technology," Chapter 7, 1998, 2nd Edition, pp. 301-335.
"Dispersants and Wetting Agents for SC and WDG," 2012, Akzo Morwet Tech Bulletin, v2, indd 1, 2 pages.
"An Introduction to Suspension Concentrates," undated, Vanderbilt Presentation, 27 pages.
International Search Report and Written Opinion issued in PCT/US2013/073128, dated Apr. 4, 2014, 12 pages.
Loughlin W.A., et al., "Investigations into the Parallel Synthesis of Novel Pyrrole-Oxazole Analogues of the Insecticide Pirate," 2006, Synthesis, 12:1975-1980, 6 pages.

(Continued)

*Primary Examiner* — Robert A Wax
*Assistant Examiner* — Thor Nielsen
(74) *Attorney, Agent, or Firm* — Senniger Powers LLP; Molly B. Edwards

(57) ABSTRACT

Provided herein are aqueous suspension concentrate compositions comprising biologically active 3,5-disubstituted-1,2,4-oxadiazoles or salts thereof that are useful, for example, in the control of nematodes. Nematodes are active, flexible, elongate organisms that live on moist surfaces or in liquid environments, including films of water within soil and moist tissues within other organisms. Many species of nematodes have evolved to be very successful parasites of plants and animals and, as a result, are responsible for significant economic losses in agriculture and livestock.

20 Claims, 14 Drawing Sheets

(56) References Cited

U.S. PATENT DOCUMENTS

2013/0303368 A1 11/2013 Slomczynska et al.
2014/0039197 A1 2/2014 Miller et al.

FOREIGN PATENT DOCUMENTS

WO 2007/145221 A1 12/2007
WO 2009/023721 A1 2/2009
WO 2012030887 A1 8/2012

OTHER PUBLICATIONS

Radspieler, A., et al., "Total Synthesis of Phorbazole C," 2001, Tetrahedron, 57:4867-4871, 5 pages.
Rudi, A., et al., "Phorbazoles A-D, Novel Chlorinated Phenylpyrrolyloxazoles from the Marine Sponge Phorbas aff. Clathrata," 1994, Tetrahedron Letters, 35/16:2589-2592, 4 pages.

* cited by examiner

Micrograph of Lot GLP 1009-20903-T (Form I)

Micrograph of Form II Lot 54478-21-4

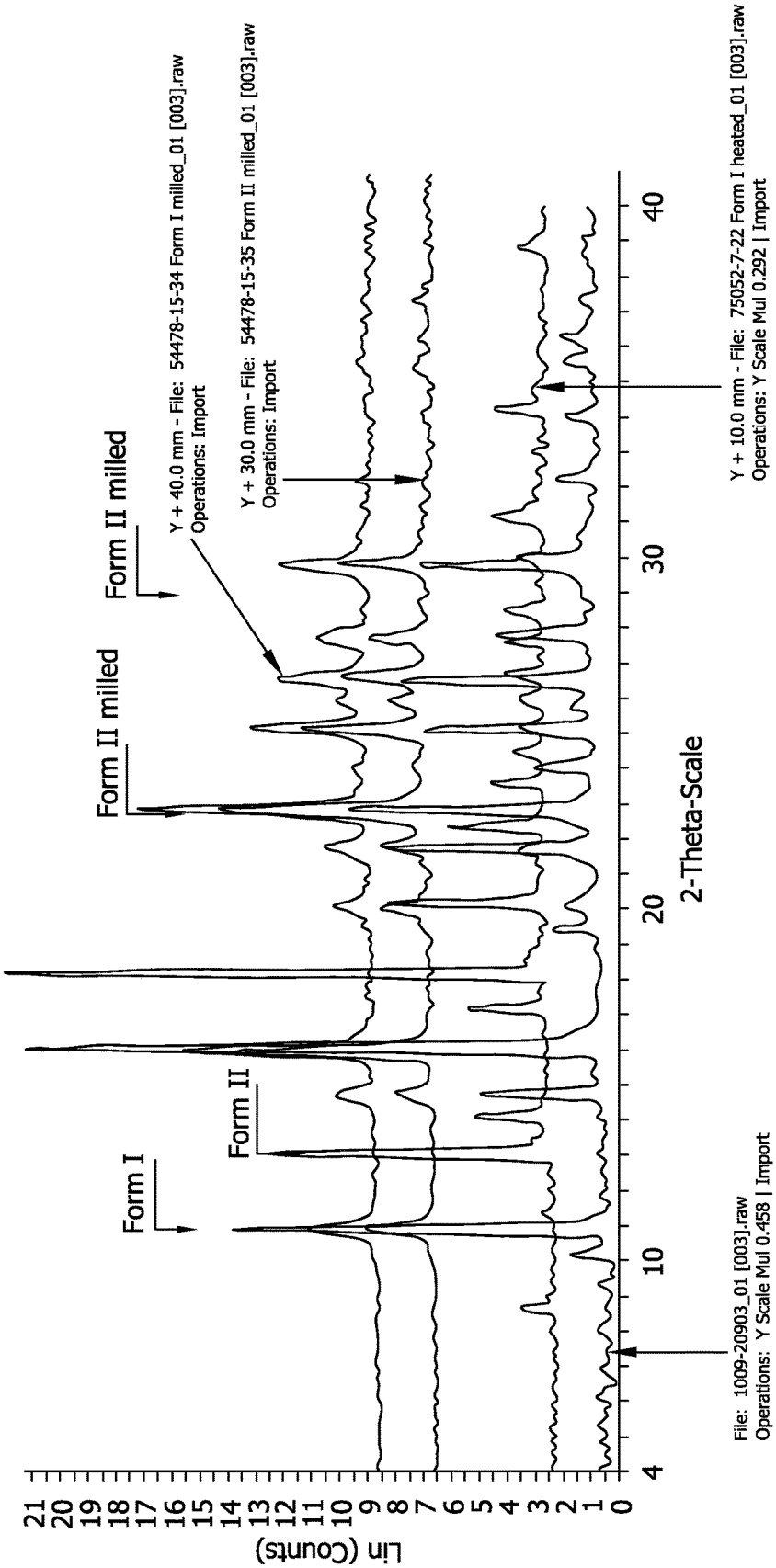

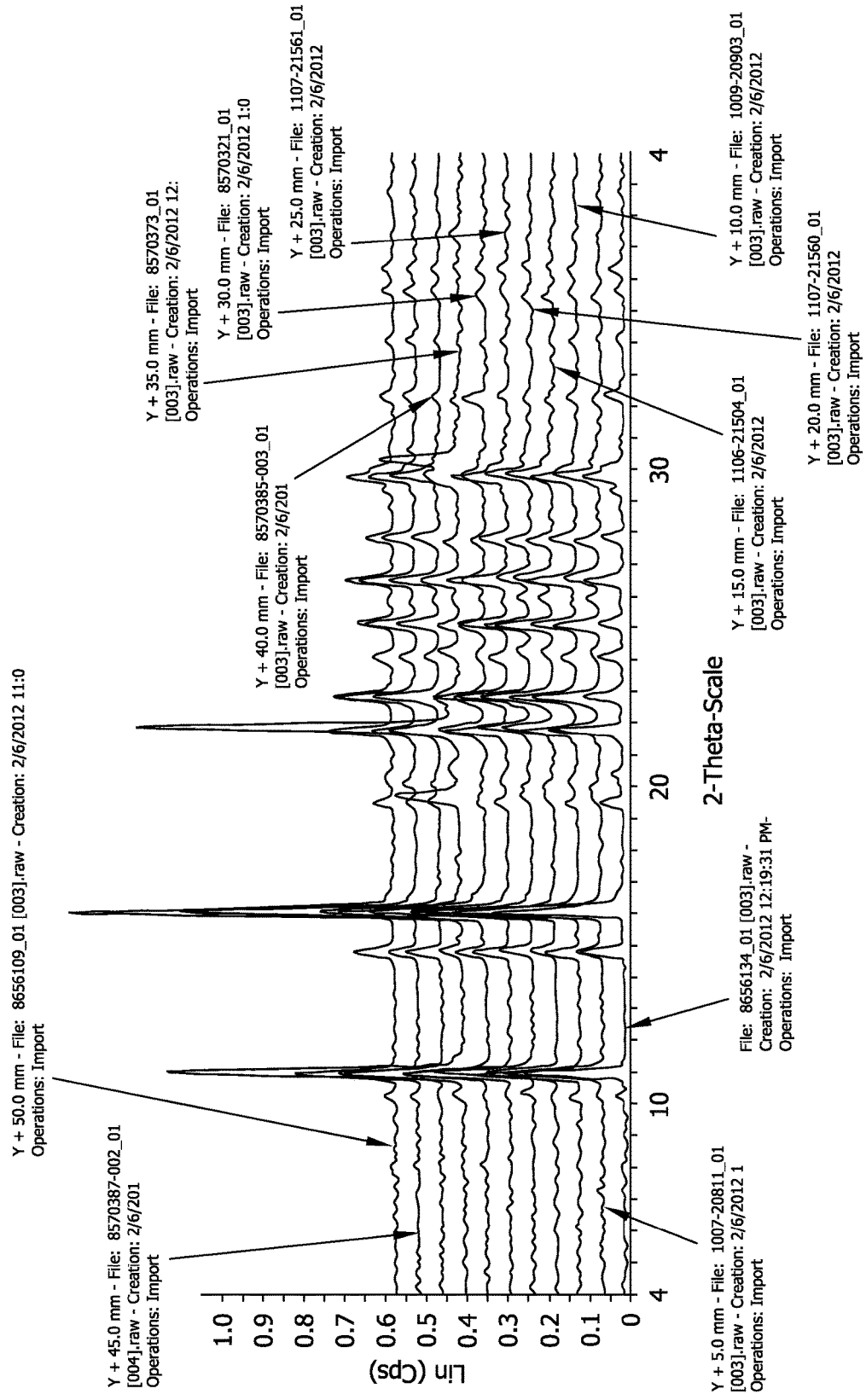

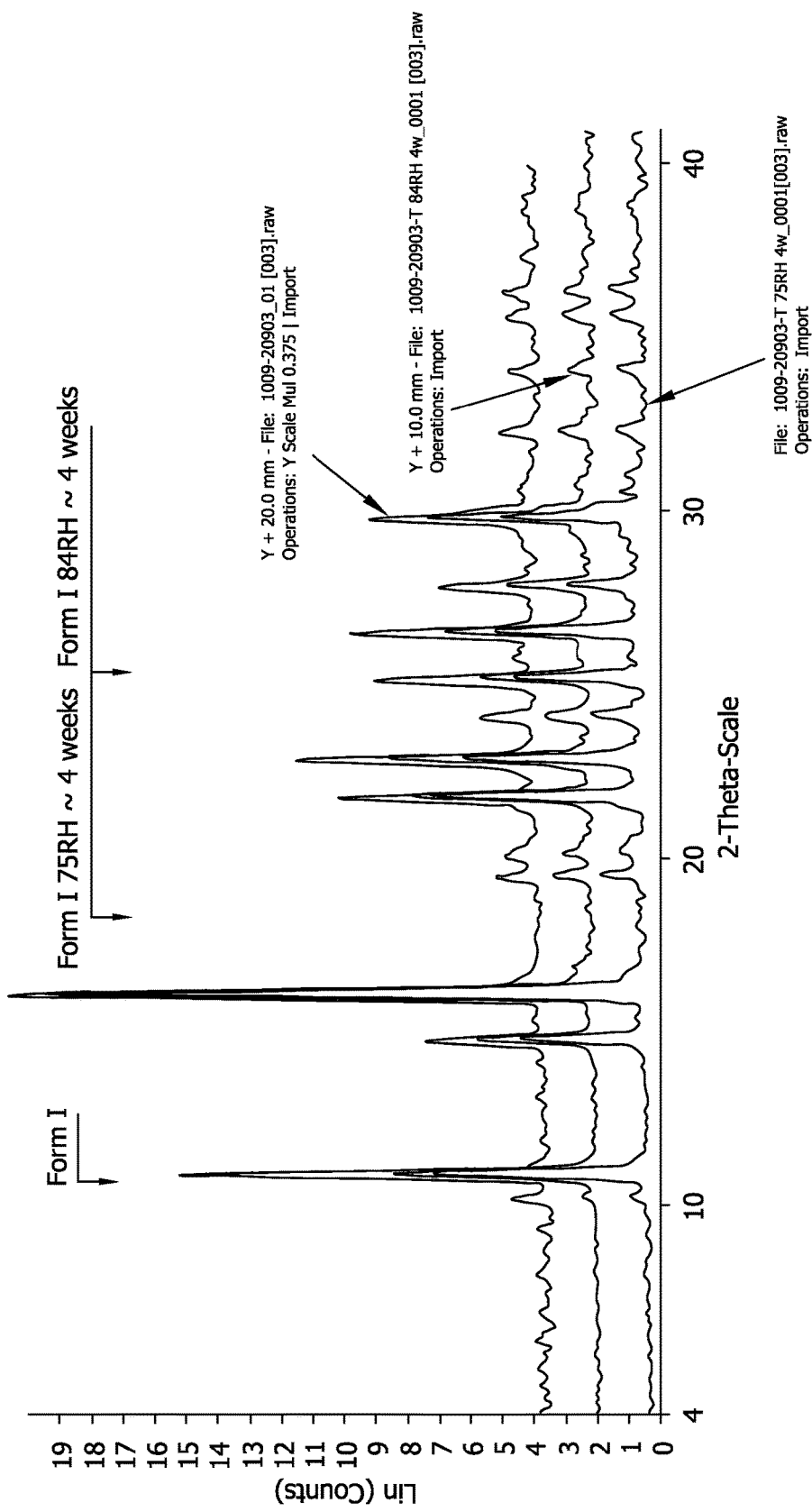

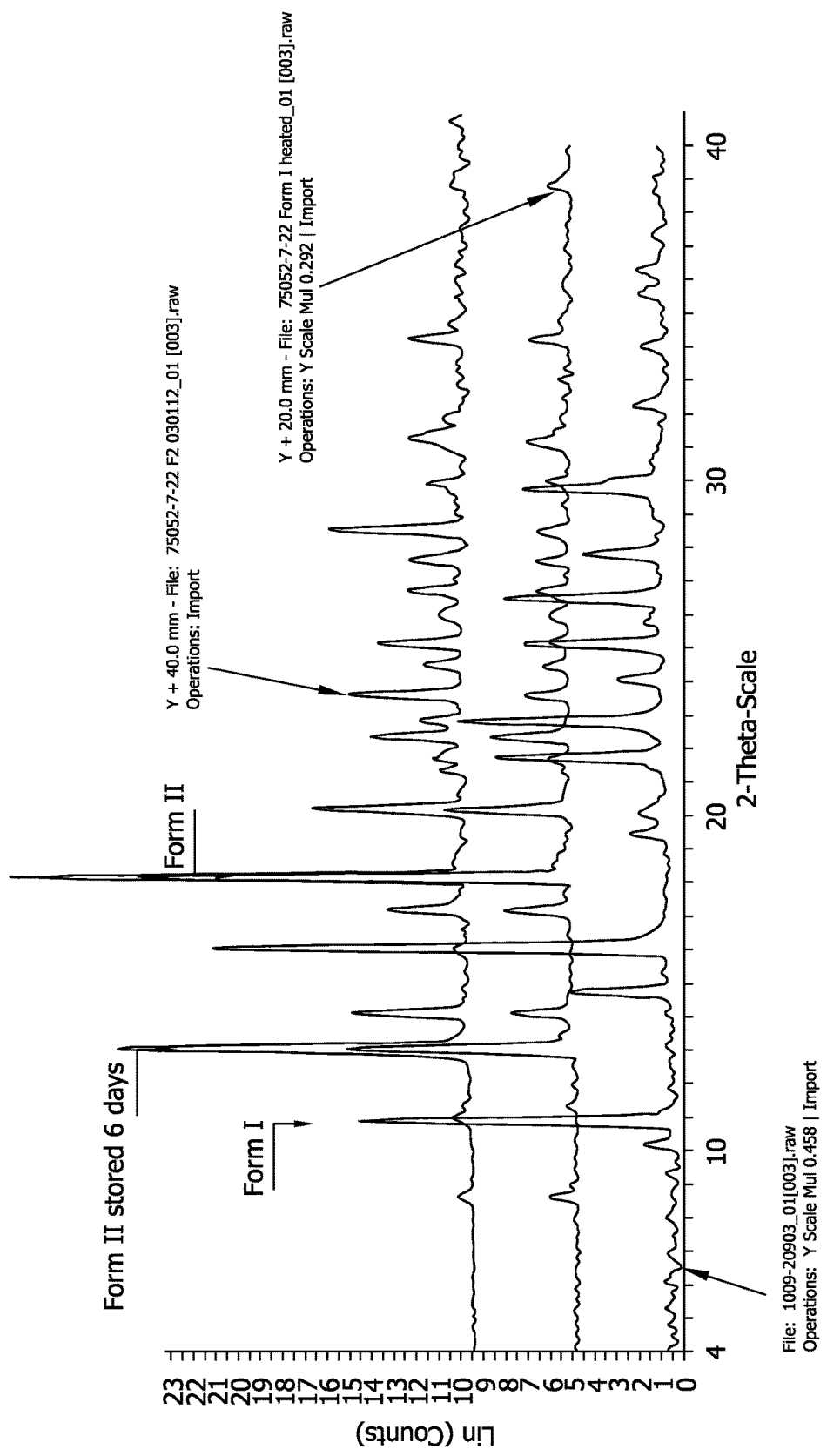

NEMATICIDAL AQUEOUS SUSPENSION CONCENTRATE COMPOSITIONS

REFERENCE TO RELATED APPLICATIONS

This application is the United States National Stage Application of International PCT Application Serial No. PCT/US2013/073128, filed Dec. 4, 2013, and claims the benefit of U.S. Provisional Application Ser. No. 61/733,239, filed Dec. 4, 2012, the entire contents of which are incorporated herein by reference.

FIELD

Provided herein are aqueous suspension concentrate compositions comprising biologically active 3,5-disubstituted-1,2,4-oxadiazoles or salts thereof that are useful, for example, in the control of nematodes.

BACKGROUND

Nematodes are active, flexible, elongate organisms that live on moist surfaces or in liquid environments, including films of water within soil and moist tissues within other organisms. Many species of nematodes have evolved to be very successful parasites of plants and animals and, as a result, are responsible for significant economic losses in agriculture and livestock.

Plant parasitic nematodes can infest all parts of the plant, including the roots, developing flower buds, leaves, and stems. Plant parasites can be classified on the basis of their feeding habits into a few broad categories: migratory ectoparasites, migratory endoparasites, and sedentary endoparasites. Sedentary endoparasites, which include root knot nematodes (*Meloidogyne*) and cyst nematodes (*Globodera* and *Heterodera*), can establish long-term infections within roots that may be very damaging to crops.

There is an urgent need in the industry for effective, economical, and environmentally safe methods of controlling nematodes. Continuing population growth, famines, and environmental degradation have heightened concern for the sustainability of agriculture.

Recently, a class of 3,5-disubstituted-1,2,4-oxadiazoles has been shown to exhibit potent, broad spectrum nematicidal activity. See generally U.S. Pat. No. 8,435,999 and U.S. Pat. No. 8,017,555, the contents of which are expressly incorporated herein by reference. The 3,5-disubstituted-1,2,4-oxadiazoles disclosed in U.S. Pat. No. 8,435,999 and U.S. Pat. No. 8,017,555 are generally characterized by low water solubility.

Two-phase suspension concentrates, which comprise solid particles of a compound suspended in an aqueous medium, are generally known in the art. In the context of seed treatment applications, suspension concentrates are known to offer several potential advantages, including high active loading, ease of handling, and reduced toxicity and flammability associated with solvents. The suspension concentrate compositions known in the art, however, are also prone to instability and settling upon storage, and may not provide a uniform distribution of the active nematicide compound in a manner that enhances bioavailability.

To be effective for use as a seed treatment composition, a nematicidal suspension concentrate desirably satisfies several key requirements. The nematicidal active ingredient must be effectively incorporated into a suspension having commercially acceptable storage stability. The suspension should exhibit acceptable storage stability over a wide temperature range and even where the nematicidal active ingredient is present in a high loading, which reduces the required volume of the composition and, therefore, reduces the expense of storage and shipping. The nematicidal active ingredient must also be amenable to transfer from the suspension concentrate to the surface of the seed, such that the desired loading can be efficiently achieved. Moreover, following application to the seed, it may be desirable for the nematicidal active ingredient to effectively migrate from the seed surface to the root zone of the surrounding soil.

Accordingly, there remains a need in the art to develop compositions that enable the efficient use of the above-mentioned potent and effective 3,5-disubstituted-1,2,4-oxadiazole nematicidal compounds in large-scale, commercial agricultural applications, particularly in seed treatment applications, to protect against nematode infestations.

SUMMARY OF THE INVENTION

In one aspect, the present invention is therefore directed to a nematicidal aqueous suspension concentrate composition, wherein the composition comprises a continuous aqueous phase comprising a dispersant component, and a dispersed solid particulate phase comprising a nematicidal component, the nematicidal component comprising a 3,5-disubstituted-1,2,4-oxadiazole compound or a salt thereof, wherein the median size of solid particulates in the dispersed solid particulate phase is less than about 10 μm.

In one embodiment, the present invention is directed to a nematicidal aqueous suspension concentrate composition as described above, wherein the nematicidal component comprises a compound of Formula (I) or a salt thereof,

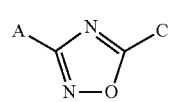

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more substituents selected from the group consisting of F, Cl, $CH_3$, and $OCF_3$.

In another embodiment, the present invention is directed to a nematicidal aqueous suspension concentrate composition as described above, wherein the nematicidal component comprises a compound of Formula (II) or a salt thereof,

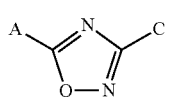

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more with substituents selected from the group consisting of F, Cl, $CH_3$, and $OCF_3$.

Another aspect of the present invention is directed to methods of preparing the nematicidal aqueous suspension concentrate compositions described above. In one embodiment, the method comprises mixing the nematicidal compound, the dispersant, and water to form an aqueous suspension; and wet milling the aqueous suspension to produce a milled suspension having a reduced particle size.

Another aspect of the present invention is directed to methods of protecting the roots of a plant against damage by a nematode, the method comprising applying a nematicidal aqueous suspension concentrate composition as described above the soil surrounding the root zone of a plant.

Another aspect of the present invention is directed to methods of protecting a seed and/or the roots of a plant grown from the seed against damage by a nematode, the method comprising treating a seed with a seed treatment composition, the seed treatment composition comprising a nematicidal aqueous suspension concentrate composition as described above.

Another aspect of the present invention is directed to a seed that has been treated with a seed treatment composition, the seed treatment composition comprising a nematicidal aqueous suspension concentrate composition as described above.

BRIEF DESCRIPTION OF THE DRAWINGS

FIG. 4 depicts an X-ray diffraction (XRD) overlay of polymorphic Forms I and II of 3-phenyl-5-(thiophen-2-yl)-1,2,4-oxadiazole.

FIG. 6 depicts the results of a powder XRD analysis of the Form I polymorph of 3-phenyl-5-(thiophen-2-yl)-1,2,4-oxadiazole.

FIG. 10 depicts the results of an XRD analysis on samples of 3-phenyl-5-(thiophen-2-yl)-1,2,4-oxadiazole material after 4 weeks of storage.

FIG. 11 depicts the XRD overlays of Forms I, II and the sample of Form II which showed signs of transformation to Form I.

DETAILED DESCRIPTION OF THE INVENTION

Figure 1:
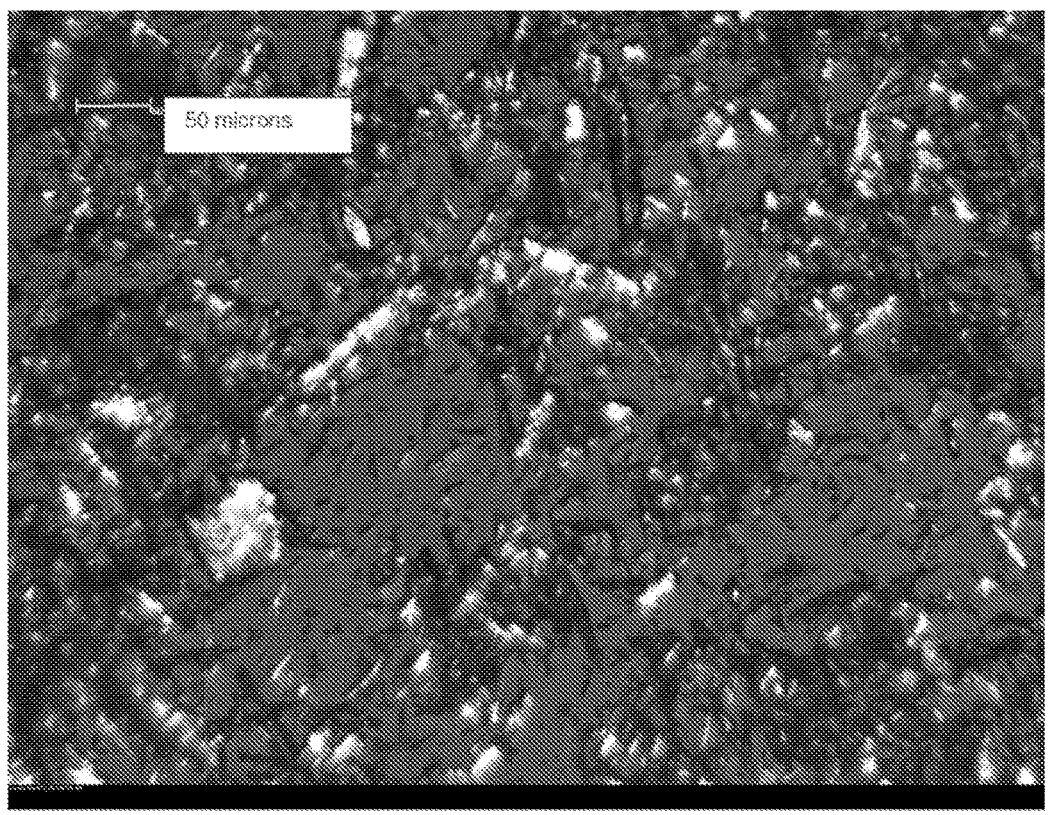
FIG. 1 depicts a representative photomicrograph of polymorphic Form I of 3-phenyl-5-(thiophen-2-yl)-1,2,4-oxadiazole.

Provided herein are aqueous suspension concentrate nematicidal compositions comprising 3,5-disubstituted-1,2,4-oxadiazoles and having improved effectiveness for seed treatment applications.

It has been discovered that the dispersibility of solid particulates of these generally hydrophobic, nematicidal compounds in an aqueous medium can be significantly increased through the application of milling techniques that substantially reduce the mean and median particle size characteristics of the dispersed solid phase, and by employing selected dispersants. The reduced size of the solid particulates enables the preparation of storage-stable, high-load suspension concentrate compositions. Increasing the aqueous dispersibility of these active nematicidal agents is highly beneficial, particularly in agricultural applications. For example, the compositions of the present invention may be advantageously applied to seeds as a prophylactic treatment against nematode infestation. Improved aqueous dispersibility provides for a more effective dispersion and more consistent loading of the nematicidal compound during initial application of the composition to the seed. In addition, the improved aqueous dispersibility provided by the present compositions is beneficial during the post-planting stage, as it allows the nematicide to more effectively disperse throughout the hydrophilic environment in the soil surrounding the seed and, subsequently, the root zone of the plant. Furthermore, it has been discovered that by controlling the particle size distribution of the nematicide particles as described herein, the adhesion characteristics of the active compound on the surface of the seeds allows for the efficient production of treated seeds having the desired active loading, and later enhances the bioavailability of the active compound in the soil.

The aqueous suspension concentrate nematicidal compositions described herein are sometimes referred to herein as "suspension concentrate compositions," or more briefly as "suspension concentrates" or "the composition." The suspension concentrate composition may also be referred to herein as a "seed treatment composition," particularly in the context of seed treatment applications.

Nematicide

The aqueous compositions described herein generally comprise a nematicide component comprising one or more 3,5-disubstituted-1,2,4-oxadiazole compounds.

For example, in one embodiment, the nematicide component comprises a compound of Formula I or a salt thereof,

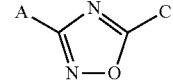

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more substituents selected from the group consisting of F, Cl, $CH_3$, and $OCF_3$.

In a more specific embodiment, the nematicide component comprises a 3,5-disubstituted-1,2,4-oxadiazole of Formula Ia or a salt thereof,

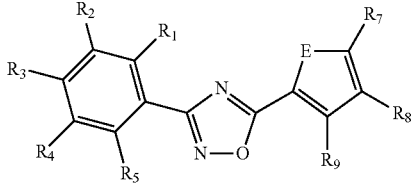

Formula Ia wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$ and $R_8$ are independently selected from hydrogen and F; $R_9$ is selected from the group consisting of hydrogen, F, Cl, $CH_3$, and $OCF_3$; and E is O, N or S. Typically, E is selected from the group consisting of O and S.

In another embodiment, the nematicide component comprises a compound of Formula Ib or a salt thereof,

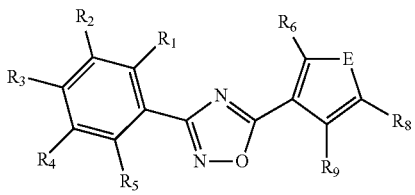

Formula Ib wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_8$ is selected from hydrogen and F; $R_6$ and $R_9$ are independently selected from the group consisting of hydrogen, F, Cl, $CH_3$, and $OCF_3$; and E is N, O or S. Typically, E is selected from the group consisting of O and S.

In another embodiment, the nematicide component comprises a 3,5-disubstituted-1,2,4-oxadiazole of Formula II or a salt thereof,

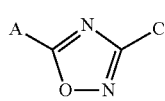

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more with substituents selected from the group consisting of F, Cl, $CH_3$, and $OCF_3$.

In a more specific embodiment, the nematicide component comprises a compound of Formula IIa or a salt thereof,

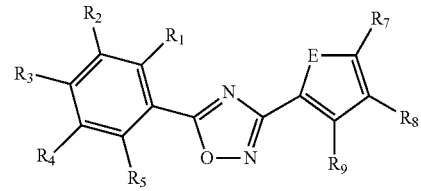

Formula IIa wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_7$ and $R_8$ are independently selected from hydrogen and F; $R_9$ is selected from the group consisting of hydrogen, F, Cl, $CH_3$, and $OCF_3$; and E is N, O or S. Typically, E is selected from the group consisting of O and S.

In another embodiment, the nematicide component comprises a compound of Formula IIb or a salt thereof,

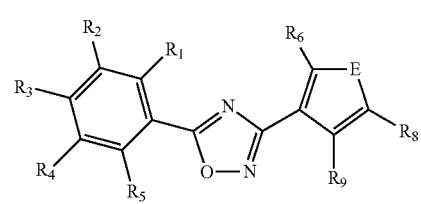

Formula IIb wherein $R_1$ and $R_5$ are independently selected from the group consisting of hydrogen, $CH_3$, F, Cl, Br, $CF_3$ and $OCF_3$; $R_2$ and $R_4$ are independently selected from the group consisting of hydrogen, F, Cl, Br, and $CF_3$; $R_3$ is selected from the group consisting of hydrogen, $CH_3$, $CF_3$, F, Cl, Br, $OCF_3$, $OCH_3$, CN, and C(H)O; $R_8$ is selected from hydrogen and F; $R_6$ and $R_9$ are independently selected from the group consisting of hydrogen, F, Cl, $CH_3$, and $OCF_3$; and E is N, O or S. Typically, E is selected from the group consisting of O and S.

In a preferred embodiment, the nematicidal component comprises a 3,5-disubstituted-1,2,4-oxadiazole of Formula (Ia) or a salt thereof. Non-limiting examples of species include 3-phenyl-5-(thiophen-2-yl)-1,2,4-oxadiazole of Formula (Ia-i),

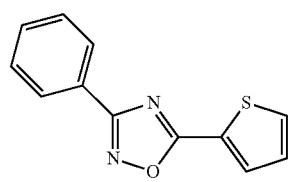

(Ia-i)

3-(4-chlorophenyl)-5-(furan-2-yl)-1,2,4-oxadiazole of Formula (Ia-ii),

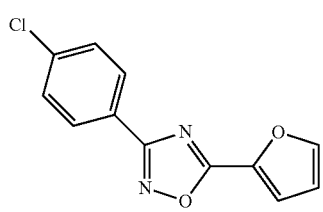

3-(4-chloro-2-methylphenyl)-5-(furan-2-yl)-1,2,4-oxadiazole of Formula (Ia-iii),

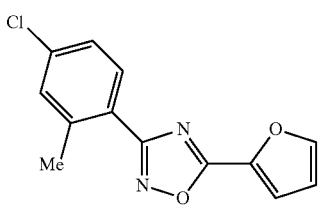

and 5-(furan-2-yl)-3-phenyl-1,2,4-oxadiazole of Formula (Ia-iv).

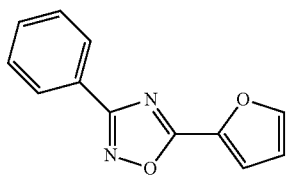

In another embodiment, the nematicidal component comprises a 3,5-disubstituted-1,2,4-oxadiazole of Formula (Ib) or a salt thereof Non-limiting examples of species include 3-(4-bromophenyl)-5-(furan-3-yl)-1,2,4-oxadiazole of Formula (Ib-i),

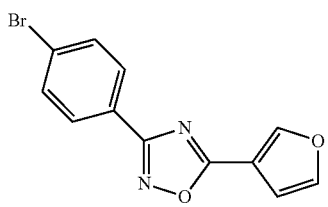

and 3-(2,4-difluorophenyl)-5-(thiophen-3-yl)-1,2,4-oxadiazole of Formula (Ib-ii).

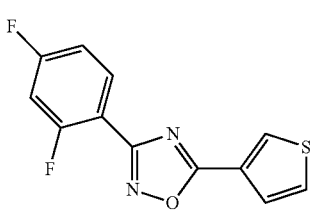

In another embodiment, the nematicidal component comprises a 3,5-disubstituted-1,2,4-oxadiazole of Formula (IIa) or a salt thereof. Non-limiting examples of species include 3-(thiophen-2-yl)-5-(p-tolyl)-1,2,4-oxadiazole of Formula (IIa-i),

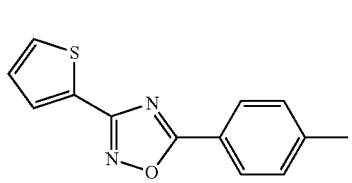

5-(3-chlorophenyl)-3-(thiophen-2-yl)-1,2,4-oxadiazole of Formula (IIa-ii),

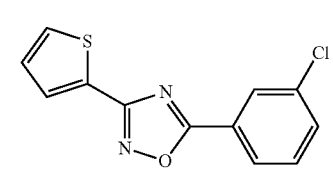

and 5-(4-chloro-2-methylphenyl)-3-(furan-2-yl)-1,2,4-oxadiazole of Formula (IIa-iii).

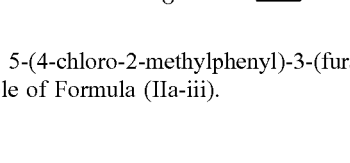

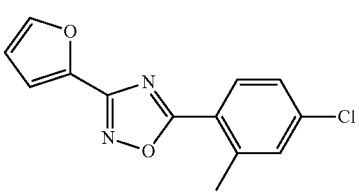

Polymorphs of the Nematicidal Compounds

The aqueous suspension concentrate composition can comprise any of the polymorphic forms of the nematicidal compounds described herein.

Generally, polymorphism refers to the potential of a chemical entity to exist in different three-dimensional arrangements in the solid state. Different polymorphic forms of a compound can have different physical properties, including: solubility and dissolution rate; crystal shape; solid state stability; batch-to-batch manufacturing reproducibility; stability; ease of formulation; and bioavailability, among others. In deciding which polymorph of a given compound is preferable for a specific application, the relevant properties of each polymorph should be determined and compared, so that the polymorph with the most desirable combination of attributes can be selected for use.

For example, it has been discovered that the nematicidal compound 3-phenyl-5-(thiophen-2-yl)-1,2,4-oxadiazole, referred to herein as the compound of Formula (Ia-i), exists in two distinct polymorphic forms, referred to herein as Form I and Form II. Form I is believed to be the thermodynamically stable form under ambient conditions, while Form II is metastable at room temperature and pressure. The polymorphs are enantiotropically related. The transition temperature between the two forms is believed to be approximately 102° C., wherein Form I is the stable form below the transition temperature, and Form II is the more thermodynamically stable form above that temperature.

Form I is believed to correspond to a dry crystalline polymorphic form of the compound. Generally, Form I does not appear to be prone to hydrate formation. Microscopic evaluation of Form I showed birefringent acicular to columnar shaped particles ranging from approximately 50 to 100 microns in length. FIG. 1 shows the representative photomicrograph at room temperature.

Figure 2:
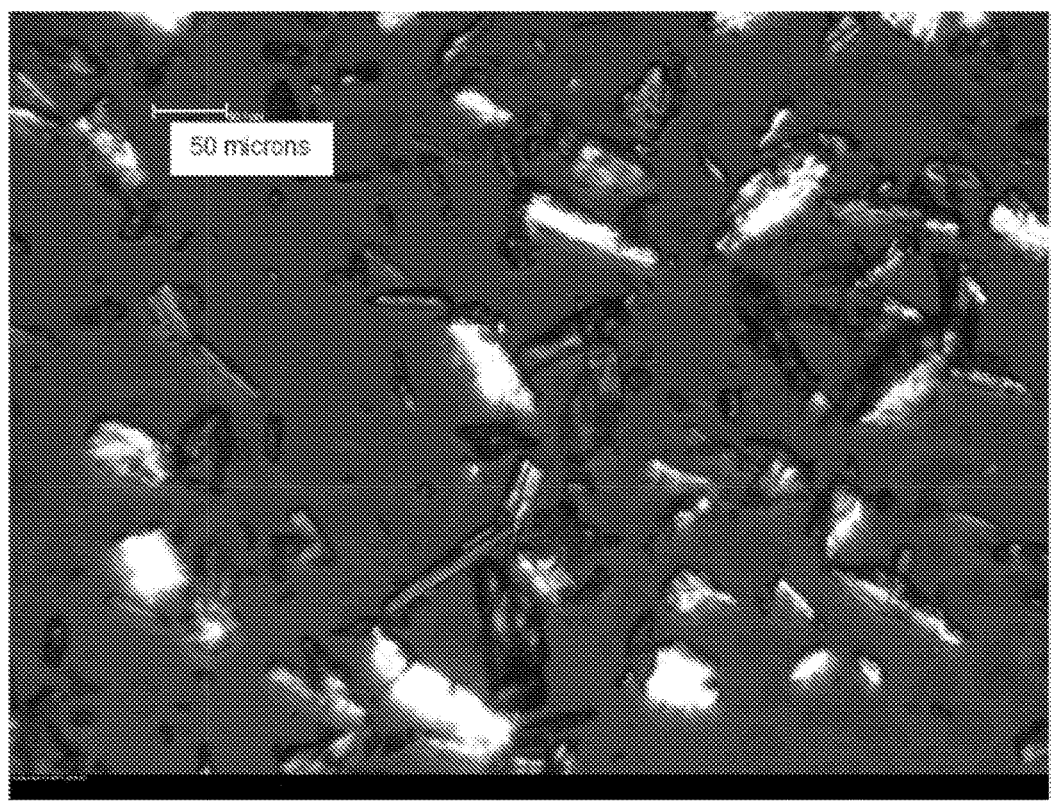
FIG. 2 depicts a representative photomicrograph of polymorphic Form II of 3-phenyl-5-(thiophen-2-yl)-1,2,4-oxadiazole.

Form II is also believed to correspond to a dry crystalline polymorphic form of the compound. Microscopic evaluation of Form II showed birefringent acicular, columnar, and flake shaped particles ranging from approximately 25 to 150 microns in length. FIG. 2 shows the representative photomicrograph at room temperature.

Generally, the aqueous suspension concentrate composition can comprise any of the polymorphic forms of the nematicidal compounds described herein. For example, in one embodiment, the suspension concentrate composition comprises polymorphic Form I of the compound of Formula (Ia-i). In another embodiment, the suspension concentrate composition comprises polymorphic Form II of the compound of Formula (Ia-i). Mixtures of more than one polymorph are also considered to be within the scope of the invention. For example, in one embodiment, the suspension concentrate composition comprises a mixture of polymorphic forms I and II of the compound of Formula (Ia-i).

Concentration

The suspension concentrate composition in some embodiments comprises at least about 10%, at least about 15%, at least about 20%, at least about 25%, at least about 30%, at least about 35%, at least about 40%, at least about 45%, or at least about 50% by weight of the nematicide component comprising one or more active nematicidal compounds as described above. In one embodiment, the suspension concentrate composition comprises at least about 40% by weight of the nematicide component. In some embodiments, the suspension concentrate composition comprises at least about 45% by weight of the nematicide component, or even higher (e.g., at least about 50% by weight).

The suspension concentrate composition comprises the nematicide component in a concentration of at least about 100 g/L, at least about 200 g/L, at least about 250 g/L, at least about 300 g/L, at least about 350 g/L, at least about 400 g/L, at least about 450 g/L, at least about 500 g/L, at least about 550 g/L, at least about 600 g/L, at least about 650 g/L, or at least about 700 g/L. The nematicide concentration ranges from about 400 g/L to about 700 g/L, from about 450 g/L to about 750 g/L, or from about 450 g/L to about 700 g/L.

Particle Size

The suspension concentrate compositions of the present invention comprise a continuous aqueous phase and a dispersed solid phase comprising solid particulates of the nematicide component as described herein. The solid nematicidal particulates have a particle size distribution selected to enhance dispersibility of the particles suspended in the composition and improve the stability of the suspension concentrate composition.

It has been discovered, however, that further reductions in particle size provide a number of benefits, including improved adhesion characteristics of the 3,5-disubstituted-1,2,4-oxadiazole compounds when the composition is applied as a seed treatment. The particle size reduction described herein provides enhanced adhesion of the nematicidal active ingredient to the seed surface when the composition is applied as a seed treatment and thereby allows for efficient production of treated seeds having a uniform active loading. Furthermore, and without being bound to a particular theory, it is believed that further reducing the particulate size of the 3,5-disubstituted-1,2,4-oxadiazole compounds facilitates improved dispersibility of the solid nematicidal active within the aqueous environment of the root zone after planting the treated seed in the soil. Dispersion of the nematicide throughout the surrounding root zone helps prevent soil nematodes from coming into contact with the seed and, later, the newly formed roots of the plant emerging from the seed, and ultimately manifests as an improvement in nematicidal efficacy (i.e., a reduction in plant damage attributable to nematodes).

In the preparation of suspension concentrates, there are considerable energy costs and time requirements associated with reducing the particle size of the solid phase. These costs tend to increase significantly as the particle size decreases. Accordingly, efficient production of suspension concentrates must take into account the additional costs and benefits associated with the particle size reduction step.

Accordingly, the particle size characteristics of the dispersed solid phase of the suspension concentrate composition comprising the 3,5-disubstituted-1,2,4-oxadiazole compounds described above are selected so as to not only provide a stable suspension, but also to allow for efficient production of treated seeds having a uniform active loading and enhanced nematicidal efficacy. More particularly, the dispersed solid phase of the suspension concentrate has a median particle size less than about 50 μm, less than 30 μm, less than 20 μm, less than 10 μm, less than about 5 μm, less than about 4 μm, less than about 3 μm, less than about 2 μm, or less than about 1 μm. The suspension concentrate composition typically has a median particle size falling within the range of from about 0.5 μm to about 10 μm, from about 1 μm to about 5 μm, from about 1 μm to about 4 μm, from about 1 μm to about 3 μm, or from about 1 μm to about 2 μm. In some embodiments, the median particle size falls within the range of from about 0.5 μm to about 5 μm, from about 0.5 μm to about 4 μm, from about 0.5 μm to about 3 μm, from about 0.5 μm to about 2 μm, or from about 0.5 μm to about 1 μm. In one embodiment, the median particle size falls within the range of from about 1 μm to about 2 μm.

The dispersed solid phase of the suspension concentrate composition typically has a mean particle size less than about 20 μm, less than about 10 μm, less than about 5 μm, less than about 4 μm, less than about 3 μm, less than about 2 μm, or less than about 1 μm. The mean particle size typically falls within the range of from about 0.5 μm to about 20 μm, from about 0.5 μm to about 10 μm, from about 1 μm to about 5 μm, from about 1 μm to about 4 μm, from about 1 μm to about 3 μm, or from about 1 μm to about 2 μm. In some embodiments, the mean particle size falls within the range of from about 0.5 μm to about 5 μm, from about 0.5 μm to about 4 μm, from about 0.5 μm to about 3 μm, from about 0.5 μm to about 2 μm, or from about 0.5 μm to about 1 μm.

The mean and/or median particle size of the solid particulates in the dispersed phase can be determined by means known in the art, including laser diffraction particle size analysis. A non-limiting example of a suitable apparatus for determining the particle size characteristics of the solid particulates is a BECKMAN COULTER LS Particle Size Analyzer (model LS 13 320).

The dispersed solid phase of the suspension concentrate typically has a polydispersity index, defined as the arithmetic mean particle size divided by the median particle size, of less than about 10. In some embodiments, the polydispersity index is less than about 5, less than about 2, or less than about 1.5. The polydispersity index typically falls within the range of from about 1 to about 2.

Dispersant

The suspension concentrate composition additionally comprises a dispersant component comprising one or more dispersants selected to enhance dispersibility of the solid particles suspended in the composition and improve the stability of the suspension concentrate composition. The dispersant may be selected from non-ionic dispersants, anionic dispersants, or cationic dispersants.

In a preferred embodiment, the dispersant is anionic. Examples of anionic dispersants include alkyl sulfates, alcohol sulfates, alcohol ether sulfates, alpha olefin sulfonates, alkylaryl ether sulfates, arylsulfonates, alkylsulfonates, alkylaryl sulfonates, sulfosuccinates, mono- or diphosphate esters of polyalkoxylated alkyl alcohols or alkyl phenols, mono- or disulfosuccinate esters of alcohols or polyalkoxylated alkanols, alcohol ether carboxylates, phenol ether carboxylates.

In one embodiment, the dispersant is an alkylaryl sulfonate. Alkylaryl sulfonates have been found to be effective at forming a stable aqueous suspension comprising the 3,5-disubstituted-1,2,4-oxadiazole compounds used in the practice of the present invention, particularly at high concentrations of the nematicidal active ingredient.

Non-limiting examples of commercially available anionic dispersants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (available from Aldrich), diphenyloxide disulfonate, naphthalene formaldehyde condensate, DOWFAX (available from Dow), dihexylsulfosuccinate, and dioctylsulfosuccinate. For example, the anionic dispersant may comprise an alkyl naphthalene sulfonate condensate or a salt thereof.

Examples of non-ionic dispersants include sorbitan esters, ethoxylated sorbitan esters, alkoxylated alkylphenols, alkoxylated alcohols, block copolymer ethers, and lanolin derivatives. In accordance with one embodiment, the dispersant comprises an alkylether block copolymer Non-limiting examples of commercially available non-ionic dispersants include SPAN 20, SPAN 40, SPAN 80, SPAN 65, and SPAN 85 (available from Aldrich); TWEEN 20, TWEEN 40, TWEEN 60, TWEEN 80, and TWEEN 85 (available from Aldrich); IGEPAL CA-210, IGEPAL CA-520, IGEPAL CA-720, IGEPAL CO-210, IGEPAL CO-520, IGEPAL CO-630, IGEPAL CO-720, IGEPAL CO-890, and IGEPAL DM-970 (available from Aldrich); Triton X-100 (available from Aldrich); BRIJ S10, BRIJ S20, BRIJ 30, BRIJ 52, BRIJ 56, BRIJ 58, BRIJ 72, BRIJ 76, BRIJ 78, BRIJ 92V, BRIJ 97, and BRIJ 98 (available from Aldrich); PLURONIC L-31, PLURONIC L-35, PLURONIC L-61, PLURONIC L-81, PLURONIC L-64, PLURONIC L-121, PLURONIC 10R5, PLURONIC 17R4, and PLURONIC 31R1 (available from Aldrich); Atlas G-5000 and Atlas G-5002 L (available from Croda); ATLOX 4912 and ATLOX 4912-SF (available from Croda); and SOLUPLUS (available from BASF), LANEXOL AWS (available from Croda).

Non-limiting examples of cationic dispersants include mono alkyl quaternary amine, fatty acid amide surfactants, amidoamine, imidazoline, and polymeric cationic surfactants.

The suspension concentrate composition comprises from about 0.5% about 20%, from about 0.5% to about 10%, from about 0.5% to about 5%, or from about 0.5% to about 8% of the dispersant component by weight. In one embodiment, the composition comprises the dispersant in an amount of from about 0.5% to about 5% by weight.

The suspension concentrate composition may comprise the dispersant in a concentration of at least about 5 g/L, at least about 10 g/L, at least about 15 g/L, at least about 20 g/L, at least about 25 g/L, at least about 30 g/L, at least about 35 g/L, at least about 40 g/L, at least about 45 g/L, or at least about 50 g/L. In some embodiments, the dispersant is present in a concentration of from about 1 to about 100 g/L, from about 5 to about 75 g/L, or more typically from about 20 to about 50 g/L.

In some embodiments, the suspension concentrate composition comprises a dispersant component comprising a primary dispersant in combination with one or more secondary dispersants. The secondary dispersant may also be referred to herein as a wetting agent. In one embodiment, the secondary dispersant comprises an alkylether block copolymer.

In one embodiment, the secondary dispersant is non-ionic when used in conjunction with an ionic primary dispersant. For example, in some embodiments, the dispersant component comprises a mixture of an anionic primary dispersant (described above) and a non-ionic (described above) secondary dispersant. In other embodiments, the dispersant component comprises a mixture of a cationic primary dispersant and a non-ionic secondary dispersant. In accordance with another embodiment, it has been found that the pairing of an anionic primary dispersant with a non-ionic secondary dispersant, in particular, imparts improved stability to the aqueous suspension concentrates described herein.

The secondary dispersant typically comprises from about 0.05% to about 10%, from about 0.5% to about 5%, from about 1% to about 5%, from about 1% to about 4%, or from about 1% to about 2.5% by weight of the composition.

The composition typically comprises a ratio of primary dispersant to secondary dispersant, on a weight basis, of from about 1:1 to about 10:1, from about 1:1 to about 5:1, and from about 2:1 to about 3:1.

Dendrimers

In some embodiments, the composition may further comprise one or more functionalized dendrimers to enhance the efficacy and/or stability of the composition. Non-limiting examples of classes of functionalized dendrimers include poly(amidoamine) (PAMAM, Generations 0-7), poly(amidoamine-organosilicone) (PAMAMOS), poly(propylene imidine) (PPI, Generations 0-5), poly(benzylethers) (Frechet-type), Arobols (Newkome type), poly(phenylacetylenes) and surface engineered dendrimers (e.g. PEGylated dendrimers, glycodendrimers, peptide funtionalized dendrimers, and galabiose-functionalized dendrimers). In some embodiments, the dendrimers comprise at least about 0.1% and up to 10% or more, or from about 1% to about 10% by weight of the composition.

Antifreeze Agents

In some embodiments, the composition may further comprise one or more antifreeze agents. In one embodiment, the antifreeze agent is an alcohol. Non-limiting examples of antifreeze agents include ethylene glycol, propylene glycol, butanediol, pentanediol, mannitol, sorbitol, and glycerol (glycerin).

The suspension concentrate composition may comprise the antifreeze agent in a concentration of at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, or at least about 80 g/L. The antifreeze agent is typically present in a concentration of from about 1 to about 150 g/L, from about 10 to about 100 g/L, or more typically from about 20 to about 80 g/L.

Antifoam Agents

In some embodiments, the composition may further comprise one or more antifoam agents. Examples of antifoam agents include organosilicone or silicone-free compounds. Non-limiting examples of commercially available antifoam products include Break-Thru OE441 (available from Evonik), Break-Thru AF9905 (available from Evonik), AGNIQUE DF 6889 (available from Cognis), AGNIQUE DFM 111S (available from Cognis), BYK-016 (available from BYK), FG-10 antifoam emulsion (available from Dow Corning), 1520-US (available from Dow Corning), 1510-US (available from Dow Corning), SAG 1538 (available from Momentive), and SAG 1572 (available from Momentive).

Buffer

In some embodiments, the composition may comprise a buffer solution that helps maintain the pH within a desired range. It has been discovered that, at a pH greater than about 10, wet milling and/or ball milling the nematicidal component described herein results in excessive clumping and/or agglomeration making the particle size reduction difficult, instability or degradation of the nematicidal component, and/or instability or degradation of the other suspension concentrate components described herein. As a result, a pH buffer may be selected to provide an aqueous suspension concentrate composition having a pH of less than 10, from about 5 to about 9, from about 6 to about 8, or about 7. Buffer solutions suitable for a variety of pH ranges are generally known in the art.

Thickener

In some embodiments, the composition may comprise a thickener (referred to hereinafter as "stabilizer") component. Examples of stabilizers include anionic polysaccharides and cellulose derivatives. In some embodiments, the stabilizer comprises a clay or a silica, or a colloidal hydrophilic silica. Non-limiting examples of commercially available stabilizers include KELZAN CC (available from Kelco), methyl cellulose, carboxymethylcellulose and 2-hydroxyethylcellulose, hydroxymethylcellulose, kaolin, and microcrystalline cellulose. A non-limiting example of a commercially available colloidal hydrophilic silica is AEROSIL (available from Evonik).

The stabilizer component typically comprises from about 0.05% to about 10% by weight of the composition. For example, in some embodiments, the stabilizer component comprises from about 0.1% to about 5%, from about 0.1% to about 2%, or from about 0.1% to about 1% by weight of the composition.

Crystal Growth Inhibitor

In some embodiments, the composition may comprise a crystal growth inhibitor. Examples of crystal growth inhibitors include acrylic copolymers, polyethylene glycol, polyethylene glycol hydrogenated castor oil and combinations. Non-limiting examples of commercially available crystal growth inhibitor include ATLOX 4913 (available from Croda).

The crystal growth inhibitor component may comprise from about 1% to about 10% by weight of the composition.

Co-Solvent

In some embodiments, the composition may further comprise a co-solvent in addition to water. Non-limiting examples of co-solvents that can be used include, ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVESSO series available from Exxon Mobil), isoparaffinic fluids (e.g. ISOPAR series, available from Exxon Mobil), cycloparaffinic fluids (e.g. NAPPAR 6, available from Exxon Mobil), mineral spirits (e.g. VARSOL series available from Exxon Mobil), and mineral oils (e.g., paraffin oil).

Non-limiting examples of preferred commercially available organic solvents include pentadecane, ISOPAR M, and ISOPAR V and ISOPAR L (available from Exxon Mobil).

Rheology Modifying Agent

In some embodiments, the composition may further comprise one or more rheology modifying agents.

Examples of rheology modifying agents include humic acid salts, fulvic acid salts, humin, and lignin salts.

In one embodiment, the rheology modifying agent is the sodium or potassium salt of humic acid. Generally, a humic substance is one produced by biodegradation of dead organic matter, particularly dead plant matter (e.g., lignin). With respect to the compositions of the present invention, it has been discovered that compositions comprising a humic acid exhibit a lower viscosity than similarly-loaded compositions in the absence of a humic acid. Fulvic acids, which are humic acids of lower molecular weight and higher oxygen content than other humic acids, are used in some embodiments.

Additional Excipients

In some embodiments, composition comprises one or more additional excipients that improve the adhesion of the composition to the seed, provide a visual indication of successful coating (e.g., coloring agents), or otherwise impart improved characteristics to the coating.

Biocidal Agents

In some embodiments, the composition may further comprise one or more biocidal agents. Typically, a biocidal component is included to prevent fungal and/or bacterial growth within the suspension concentrate composition, particularly when the composition is placed into storage. Examples of biocidal agents include dichlorophen or benzyl alcohol hemiformal based compounds, benzoisothiazolinones and rhamnolipids. Non-limiting examples of commercially available biocidal agents include ACTICIDE (available from THOR), PROXEL (available from Arch Chemical), and ZONIX (available from Jeneil).

Additional Active Ingredients

In some embodiments, the composition may be formulated, mixed in a seed treater tank or combined on the seed by overcoating with one or more additional active ingredients in combination with the nematicidal 3,5-disubstituted-1,2,4-oxadiazoles described herein.

The additional active ingredient may be, for example, an additional pesticide. The pesticide may be, for example, an insecticide, a fungicide, an herbicide, or an additional nematicide.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In particular embodiments insecticides and nematicides include abamectin, aldicarb, aldoxycarb, bifenthrin, carbofuran, chlorantraniliprole, clothianidin, clothianidin and a *Bacillus firmus*, cyantraniliprole, cyfluthrin, cyhalothrin, cypermethrin, deltamethrin, dinotefuran, emamectin, ethiprole, fenamiphos, fipronil, flubendiamide, fluopyram, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb, Non-limiting examples of useful fungicides include aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides, and triazoles. Particular examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

Non-limiting examples of herbicides include ACCase inhibitors, acetanilides, AHAS inhibitors, carotenoid biosynthesis inhibitors, EPSPS inhibitors, glutamine synthetase inhibitors, PPO inhibitors, PS II inhibitors, and synthetic auxins, Particular examples of herbicides include acetochlor, clethodim, dicamba, flumioxazin, fomesafen, glyphosate, glufosinate, mesotrione, quizalofop, saflufenacil, sulcotrione, and 2,4-D.

Additional actives may also comprise substances such as, biological control agents, microbial extracts, natural products, plant growth activators or plant defense agents. Non-limiting examples of biological control agents include bacteria, fungi, beneficial nematodes, and viruses.

In certain embodiments, the biological control agent can be a bacterium of the genus *Actinomycetes, Agrobacterium, Arthrobacter, Alcaligenes, Aureobacterium, Azobacter, Beijerinckia, Brevibacillus, Burkholderia, Chromobacterium, Clostridium, Clavibacter, Comomonas, Corynebacterium, Curtobacterium, Enterobacter, Flavobacterium, Gluconobacter, Hydrogenophage, Klebsiella, Methylobacterium, Paenibacillus, Pasteuria, Phingobacterium, Photorhabdus, Phyllobacterium, Pseudomonas, Rhizobium, Serratia, Stenotrophomonas, Variovorax*, and *Xenorhabdus*. In particular embodiments the bacteria is selected from the group consisting of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage*, and *Pseudomona fluorescens*.

In certain embodiments the biological control agent can be a fungus of the genus *Alternaria, Ampelomyces, Aspergillus, Aureobasidium, Beauveria, Colletotrichum, Coniothyrium, Gliocladium, Metarhisium, Muscodor, Paecilonyces, Trichoderma, Typhula, Ulocladium*, and *Verticilium*. In particular embodiments the fungus is *Beauveria bassiana, Coniothyrium minitans, Gliocladium virens, Muscodor albus, Paecilomyces lilacinus*, or *Trichoderma polysporum*.

In further embodiments the biological control agents can be plant growth activators or plant defense agents including, but not limited to harpin, *Reynoutria sachalinensis*, jasmonate, lipochitooligosaccharides, gibberellic acid, and isoflavones.

Methods of Preparation

Another aspect of the present invention is directed to methods of preparing the nematicidal suspension concentrate compositions described herein.

As described above, it has been discovered that significant benefits in the aqueous dispersibility of 3,5-disubstituted-1, 2,4-oxadiazoles can be obtained and other advantages realized by reducing the particulate size of the solid phase in the suspension concentrate composition. Generally, the particulate size of the nematicide component may be reduced by any method known in the art. In accordance with one preferred embodiment, the particle size of the nematicide component is reduced by wet milling. Additionally, air milling, high pressure homogenization, spinning disc, grinding and solvent evaporation techniques can be used to reduce the particle size of the nematicide component.

Typically, the first step in the process comprises a premilling step wherein the nematicidal component comprising one or more active nematicidal compounds is combined with water and agitated to form an aqueous suspension. Typically, the dispersant is also added to the aqueous suspension prior to the particle size reduction step and acts as a wet-milling aid. Other optional components which may be added to the aqueous suspension before the particle size reduction step include a secondary dispersant and/or an antifreeze agent, each of which may be selected as described above. Additionally, in one embodiment, a buffer solution is added to the suspension prior to the particle size reduction step; as discussed above, the pH of the suspension during the particle size reduction step is preferably less than 10 in order to minimize excessive clumping and/or agglomeration making the particle size reduction difficult, instability or degradation of the nematicidal component, and/or instability or degradation of the other suspension concentrate components described herein.

The aqueous suspension is then wet-milled to obtain a suspension concentrate having the desired particle size distribution as described above. The wet-milling process may be carried out using techniques and apparatus known in the art. Ball milling is a particularly preferred technique, wherein the aqueous suspension is placed inside a rotating cylinder containing grinding media. The grinding media are preferably selected from the group consisting of stainless steel beads, zirconium oxide beads, glass beads and ceramic beads. Non-limiting examples of suitable ball milling apparatus include a SIZEGVARI ATTRITOR milling system made by UNION PROCESS, and a MINI ZETA II milling machine made by Netzsch.

The wet-milling step typically produces a fine suspension comprising a dispersed solid phase having a particle size distribution characterized by the median and mean particle sizes and polydispersity index described above. Using laser diffraction particle size analysis or other suitable means, the duration and intensity of the wet-milling operation is controlled to provide a suspension concentrate composition having the desired particle size characteristics.

Following the particle size reduction, the milled aqueous suspension may be combined with an optional stabilizer component and/or one or more additional biocidal agents, each of which may be selected as described above.

Storage Stability

In one embodiment, the aqueous suspension concentrate composition described herein exhibits commercially acceptable storage stability across a wide range of temperatures and environmental conditions. In this context, storage stability is generally defined as the absence of sedimentation and the lack of any significant change in the rheological properties of the composition (e.g., viscosity). Commercially acceptable storage stability can be reliably achieved by selecting the various components of the aqueous suspension concentrate, particularly the primary dispersant, optional secondary dispersant, and/or optional stabilizer component, in accordance with the respective embodiments described in detail above. The suspension concentrate composition may be storage-stable at 25° C. for at least about 1 week, at least about 2 weeks, at least about 1 month, at least about 2 months, at least about 3 months, at least about 6 months, at least about 12 months or at least about 18 months.

Methods of Application

Another aspect of the present invention is directed to methods for protecting the roots of a plant against damage by nematodes.

Application to Seeds

In one embodiment, the method comprises protecting a seed, and/or the roots of a plant grown from the seed, against damage by a nematode by treating the seed with a seed treatment composition described herein and diluted as necessary to attain the desired nematicide compound loading on the treated seeds.

The methods described herein can be used in connection with any species of plant and/or the seeds thereof. In preferred embodiments, however, the methods are used in connection with seeds of plant species that are agronomically important. In particular, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporate a transgenic event that confers, for example, tolerance to a particular herbicide or combination of herbicides, increased disease resistance, enhanced tolerance to stress and/or enhanced yield. Transgenic seeds include, but are not limited to, seeds of corn, soybean and cotton.

In one embodiment, the treatment composition is applied to the seed prior to sowing the seed so that the sowing operation is simplified. In this manner, seeds can be treated, for example, at a central location and then dispersed for planting. This permits the person who plants the seeds to avoid the complexity and effort associated with handling and applying the seed treatment compositions, and to merely handle and plant the treated seeds in a manner that is conventional for regular untreated seeds.

The seed treatment composition can be applied to seeds by any standard seed treatment methodology, including but not limited to mixing in a container (e.g., a bottle or bag), mechanical application, tumbling, spraying, immersion, and solid matrix priming Seed coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017, among others. Any conventional active or inert material can be used for contacting seeds with the seed treatment composition, such as conventional film-coating materials including but not limited to water-based film coating materials.

For example, in one embodiment, a seed treatment composition can be introduced onto or into a seed by use of solid matrix priming. For example, a quantity of the seed treatment composition can be mixed with a solid matrix material and then the seed can be placed into contact with the solid matrix material for a period to allow the seed treatment composition to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, talc, mica, soil, sand, polyurea, polyacrylate, or any other material capable of absorbing or adsorbing the seed treatment composition for a time and releasing the nematicide of the seed treatment composition into or onto the seed. It is useful to make sure that the nematicide and the solid matrix material are compatible with each other. For example, the solid matrix material should be chosen so that it can release the nematicide at a reasonable rate, for example over a period of minutes, hours, days, or weeks.

Imbibition is another method of treating seed with the seed treatment composition. For example, a plant seed can be directly immersed for a period of time in the seed treatment composition. During the period that the seed is immersed, the seed takes up, or imbibes, a portion of the seed treatment composition. Optionally, the mixture of plant seed and the seed treatment composition can be agitated, for example by shaking, rolling, tumbling, or other means. After imbibition, the seed can be separated from the seed treatment composition and optionally dried, for example by patting or air drying.

The seed treatment composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are generally known in the art.

If the seed treatment composition is applied to the seed in the form of a coating, the seeds can be coated using a variety of methods known in the art. For example, the coating process can comprise spraying the seed treatment composition onto the seed while agitating the seed in an appropriate piece of equipment such as a tumbler or a pan granulator.

In one embodiment, when coating seed on a large scale (for example a commercial scale), the seed coating may be applied using a continuous process. Typically, seed is introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the nematicide and/or other active ingredients in the treatment composition, the desired concentration on the finished seed, and the like. The treatment composition can be applied to the seed by a variety of means, for example by a spray nozzle or revolving disc. The amount of liquid is typically determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the treatment composition. After coating, the seed can optionally be dried, for example on a tray.

In some embodiments, the treated seeds may also be enveloped with a film overcoating to protect the nematicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Application to Soil

In another aspect of the present invention, the nematicidal treatment composition, diluted as necessary to attain the desired nematicide compound loading, is directly applied to the soil surrounding the root zone of a plant. The application may be performed using any method or apparatus known in the art, including using pressurized spray application to the soil surface or injected in the planting furrow, as well as chemigation via overhead sprinkler or drip systems, transplant water treatments, and plant or root dips prior to planting. The rates used for the suspension concentrate formulations for soil application may require 0.5 to 2 kgs per hectare on a broadcast basis (rate per treated area if broadcast or banded).

Treated Seeds

Another aspect of the present invention is directed to a seed that has been treated with a nematicidal seed treatment composition as described herein. Typically, the seed has been treated with the seed treatment composition using one of the seed treatment methods set forth above, including but not limited to solid matrix priming, imbibition, coating, and spraying. The seed may be of any plant species, as described above.

Typically, the treated seeds comprise the nematicidal compound in an amount of at least about 0.05 mg/seed, more typically from about 0.05 to about 1 mg/seed, and even more typically from about 0.05 to about 0.5 mg/seed.

In some embodiments, wherein the composition comprises a paraffinic hydrocarbon solvent, the loading of active ingredient per treated seed can be significantly reduced without compromising nematicidal efficacy. For example, when the seed treatment composition comprises a paraffinic hydrocarbon solvent, the treated seeds may comprise the nematicidal compound in an amount of less than about 0.2 mg/seed, in an amount of about 0.1 mg/seed, from about 0.01 to about 0.2 mg/seed, or from about 0.02 to about 0.08 mg/seed.

The following examples are to be considered as merely illustrative, and are not intended to limit the scope of this invention.

EXAMPLES

Several active nematicidal compounds were combined with selected dispersants and other excipients and used in preparation of suspension concentrate compositions in the following examples. The nematicidal compounds are identified in Table 1.

TABLE 1

| Ia-i | 3-phenyl-5-(thiophen-2-yl)-1,2,4-oxadiazole | 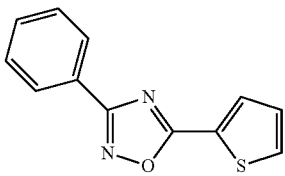 [SMILES: c1ccc(-c2noc(-c3cccs3)n2)cc1] |
| Ia-ii | 3-(4-chlorophenyl)-5-(furan-2-yl)-1,2,4-oxadiazole | 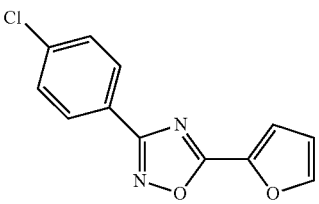 [SMILES: Clc1ccc(-c2noc(-c3ccco3)n2)cc1] |
| Ia-iii | 3-(4-chloro-2-methylphenyl)-5-(furan-2-yl)-1,2,4-oxadiazole | 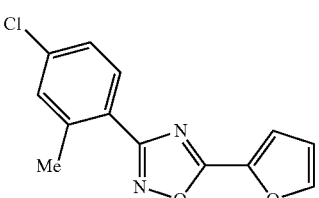 |

Example 1: Preparation of a suspension concentrate comprising 3-phenyl-5-(thiophen-2-yl)-1,2,4-oxadiazole (Ia-i)

A quantity of the nematicidal compound Ia-i (25.00 g) was added to an aqueous solution of water (25.00 g), glycerin (2.15 g), MORWET D-500 dispersant (0.32 g), and AGNIQUE DF 6889 antifoam agent (0.05 g). The resulting mixture was milled with a SIZEGVARI ATTRITOR milling system made by UNION PROCESS containing stainless steel beads having a diameter of ⅛ inch in a 100 mL jacketed metal container. The stirring speed was controlled by a VARIAC variable autotransformer.

After milling the mixture for 1 hour 40 minutes at a speed of 50 v/140 v, a white aqueous suspension (45.25 g) was collected. The particle size characteristics of the suspension were analyzed with a BECKMAN COULTER LS Particle Size Analyzer (model LS 13 320). The results indicated a mean particle size of 4.896 μm, with a median particle size of 2.937 μm. The suspension was determined to contain 47.6% (w/w) of the Ia-i nematicide.

Example 2: Preparation of a Suspension Concentrate Comprising 3-phenyl-5-(thiophen-2-yl)-1,2,4-oxadiazole (Ia-i)

A quantity of the nematicidal compound Ia-i (30.00 g) was added to an aqueous solution of water (25.00 g), glycerin (3.00 g), MORWET D-500 dispersant (0.60 g), and AGNIQUE DF 6889 antifoam agent (0.05 g). The resulting mixture was milled with a SIZEGVARI ATTRITOR milling system made by UNION PROCESS containing stainless steel beads having a diameter of ⅛ inch in a 100 mL jacketed metal container. The stirring speed was controlled by a VARIAC variable autotransformer.

After milling the mixture for 1 hour 30 minutes at a speed of 50 v/140 v, and an additional 2 hours 15 minutes at 40 v/140 v, a white aqueous suspension (45.20 g) was collected. The suspension was determined to contain 51.2% (w/w) of the Ia-i nematicide.

Example 3: Preparation of a suspension concentrate comprising 3-(4-chlorophenyl)-5-(furan-2-yl)-1,2,4-oxadiazole (Ia-ii)

A quantity of the nematicidal compound Ia-ii (34.00 g) was added to an aqueous solution of water (25.00 g), glycerin (3.00 g), MORWET D-500 dispersant (0.60 g), and AGNIQUE DF 6889 antifoam agent (0.10 g). The resulting mixture was milled with a SIZEGVARI ATTRITOR milling system made by UNION PROCESS containing stainless steel beads having a diameter of ⅛ inch in a 100 mL jacketed metal container. The stirring speed was controlled by a VARIAC variable autotransformer.

After milling the mixture for 4 hours at a speed of 50 v/140 v, a white aqueous suspension (45.40 g) was collected. The particle size characteristics of the suspension were analyzed with a BECKMAN COULTER LS Particle Size Analyzer (model LS 13 320). The results indicated a mean particle size of 4.58 µm, with a median particle size of 3.14 µm. The suspension was determined to contain 54.2% (w/w) of the Ia-ii nematicide.

Example 4: Preparation of a Suspension Concentrate Comprising 3-(4-chloro-2-methylphenyl)-5-(furan-2-yl)-1,2,4-oxadiazole (Ia-iii)

A quantity of the nematicidal compound Ia-iii (34.00 g) was added to an aqueous solution of water (25.00 g), glycerin (3.00 g), MORWET D-500 dispersant (0.60 g), and AGNIQUE DF 6889 antifoam agent (0.05 g). The resulting mixture was milled with a SIZEGVARI ATTRITOR milling system made by UNION PROCESS containing stainless steel beads having a diameter of ⅛ inch in a 100 mL jacketed metal container. The stirring speed was controlled by a VARIAC variable autotransformer.

After milling the mixture for 4 hours at a speed of 50 v/140 v, a white aqueous suspension (49.10 g) was collected. The particle size characteristics of the suspension were analyzed with a BECKMAN COULTER LS Particle Size Analyzer (model LS 13 320). The results indicated a mean particle size of 3.217 µm, with a median particle size of 2.192 µm. The suspension was determined to contain 54.2% (w/w) of the Ia-iii nematicide.

Example 5: Preparation of a Suspension Concentrate Comprising 3-(4-chlorophenyl)-5-(furan-2-yl)-1,2,4-oxadiazole (Ia-ii)

A quantity of the nematicidal compound Ia-ii (34.00 g) was added to an aqueous solution of water (141.67 g), glycerin (17.00 g), and MORWET D-500 dispersant (3.40 g). The resulting mixture was milled with a SIZEGVARI ATTRITOR milling system made by UNION PROCESS containing stainless steel beads having a diameter of ⅛ inch in a 500 mL jacketed metal container. The stirring speed was controlled by a VARIAC variable autotransformer.

After milling the mixture for 1 hour at a speed of 75 v/140 v, a small amount of AGNIQUE DF 6889 antifoam agent (0.10 g) was added. The mixture was then further stirred at 75 v/140 v for 45 minutes, and at 60 v/140 v for an additional 1 hour 45 minutes.

Following the milling process, a white aqueous suspension (330.5 g) was collected from the container. The particle size characteristics of the suspension were analyzed with a BECKMAN COULTER LS Particle Size Analyzer (model LS 13 320). The results indicated a mean particle size of 2.90 µm, with a median particle size of 1.74 µm. The suspension was determined to contain 52.8% (w/w) of the Ia-ii nematicide.

Example 6: Preparation of a Suspension Concentrate Comprising 3-phenyl-5-(thiophen-2-yl)-1,2,4-oxadiazole (Ia-i)

A quantity of the nematicidal compound Ia-i (34.00 g) was added to an aqueous solution of water (141.67 g), glycerin (17.00 g), and MORWET D-500 dispersant (3.40 g). The resulting mixture was milled with a SIZEGVARI ATTRITOR milling system made by UNION PROCESS containing stainless steel beads having a diameter of ⅛ inch in a 500 mL jacketed metal container. The stirring speed was controlled by a VARIAC variable autotransformer.

After milling the mixture for 1 hour at a speed of 75 v/140 v, a small amount of AGNIQUE DF 6889 antifoam agent (0.10 g) was added. The mixture was then further milled at 75 v/140 v for 45 minutes and at 60 v/140 v for an additional 1 hour 45 minutes.

Following the milling process, a white aqueous suspension (305.3 g) was collected from the container. The particle size characteristics of the suspension were analyzed with a BECKMAN COULTER LS Particle Size Analyzer (model LS 13 320). The results indicated a mean particle size of 3.334 µm, with a median particle size of 2.071 µm. The suspension was determined to contain 52.8% (w/w) of the Ia-i nematicide.

Example 7: Effect of Milling Time on the Mean/Median Particle Size Diameter of a Suspension Concentrate Comprising 3-phenyl-5-(thiophen-2-yl)-1,2,4-oxadiazole (Ia-i)

A quantity of the nematicidal compound Ia-i (362.4 g) was added to an aqueous solution of water (283.34 g), glycerin (34.00 g), and MORWET D-500 dispersant (6.80 g). The resulting mixture was pre-milled with a dissolver apparatus at 1900 rpm for 20 minutes. A portion of the resulting pre-milled slurry (60% of the total volume) was added to a NETZSCH MINI ZETA II milling machine filled with zirconium beads having a diameter of 1.6-2 mm. The slurry was milled for 1 hour, after which a sample of the resulting white slurry (250 g) was collected.

During the milling process, samples were periodically extracted for analysis using a BECKMAN COULTER LS Particle Size Analyzer (model LS 13 320). The resulting mean and median particle diameters for each sample are summarized in Table 2 below:

TABLE 2

| Milling Time (mins) | Mean (μm) | Median (μm) | Mean/Median |
|---|---|---|---|
| 15 | 4.073 | 2.834 | 1.437 |
| 30 | 3.041 | 2.062 | 1.475 |
| 45 | 2.872 | 1.851 | 1.551 |
| 60 | 2.781 | 1.760 | 1.580 |

The final suspension was determined to contain 44.2% (w/w) of the Ia-i nematicide. This example demonstrates that the mean and/or median particle size of the formulation can be controlled as a function of the total milling time.

Example 8: Preparation of Seed Treatment Compositions

Seed treatment compositions were prepared using the suspension concentrate compositions prepared in Examples 2-4 above.

Composition 1: A seed treatment composition comprising the nematicidal compound Ia-i was prepared by mixing a portion of the composition prepared in Example 2 (8.00 g) with CF CLEAR seed coat polymer (0.30 g), BECKER-UNDERWOOD seed gloss (1.00 g), and BECKER-UNDERWOOD red color coating (2.00 g).

Composition 2: A seed treatment composition comprising the nematicidal compound Ia-iii was prepared by mixing a portion of the composition prepared in Example 3 (18.40 g) with CF CLEAR seed coat polymer (0.69 g), BECKER-UNDERWOOD seed gloss (2.30 g), and BECKER-UNDERWOOD red color coating (4.60 g).

Composition 3: A seed treatment composition comprising the nematicidal compound Ia-ii was prepared by mixing a portion of the composition prepared in Example 4 (18.40 g) with CF CLEAR seed coat polymer (0.69 g), BECKER-UNDERWOOD seed gloss (2.30 g), and BECKER-UNDERWOOD red color coating (4.60 g).

Example 9: Treatment of Seeds with Nematicidal Compositions

Soybean seeds (2.2 kg) were added to a WILLY NIKLAUS GMBH seed treating apparatus. The seeds were tumbled inside the treater while a quantity of seed treatment formulation was added. To ensure full dispersion of the treatment composition, seeds were allowed to tumble for an additional 30 seconds before being collected.

The amount of seed treatment composition used in each prepared sample was varied in accordance with the targeted amount of active ingredient per seed. As shown in the table below, the targeted amount ranged from 0.1 to 0.5 mg/seed for Ia-i, and from 0.1 to 1 mg/seed for Ia-iii and Ia-ii. The actual amount of active ingredient per seed was analyzed upon removal from the seed treatment apparatus. The results are summarized in the table below, where the "Composition No." refers to the compositions 1-3 prepared in Example 8.

TABLE 3

| Composition No. | Active Ingredient | Targeted Active Loading (mg/seed) | Actual Active Loading (mg/seed) | Amount of Composition (g) |
|---|---|---|---|---|
| 1 | Ia-i | 0.1 | 0.07 | 0.98 |
| 1 | Ia-i | 0.3 | 0.22 | 2.94 |
| 1 | Ia-i | 0.5 | 0.37 | 4.90 |
| 3 | Ia-ii | 0.1 | 0.07 | 0.92 |
| 3 | Ia-ii | 0.3 | 0.25 | 2.77 |

TABLE 3-continued

| Composition No. | Active Ingredient | Targeted Active Loading (mg/seed) | Actual Active Loading (mg/seed) | Amount of Composition (g) |
|---|---|---|---|---|
| 3 | Ia-ii | 0.5 | 0.46 | 4.62 |
| 3 | Ia-ii | 0.0 | 0.83 | 9.24 |
| 2 | Ia-iii | 0.1 | 0.04 | 0.92 |
| 2 | Ia-iii | 0.3 | 0.21 | 2.77 |
| 2 | Ia-iii | 0.5 | 0.40 | 4.62 |
| 2 | Ia-iii | 0.0 | 0.65 | 9.24 |

The results indicate that, for each sample, a significant portion of the active nematicidal ingredient added to the seed treatment apparatus was successfully transferred to the seed.

Example 10: Preparation of Suspension Concentrate Compositions

An additional series of suspension concentrate compositions were prepared using the procedures set forth below.

A stock buffer solution was prepared by adding anhydrous monobasic potassium phosphate (9.361 g) and dibasic sodium phosphate heptahydrate (32.732 g) to a 1 liter volumetric flask, the balance of which was filled with deionized water. The flask was shaken until the salts were fully dissolved, providing a clear buffer solution with a pH of 7.

For each sample, a blank solution was then prepared by combining MORWET D-425 dispersant, PLURONIC L-35 secondary dispersant, propylene glycol, and a quantity of the stock buffer solution as prepared above. The relative proportions of these components in each sample, respectively, are provided in Table 4 below.

In the next step of the process, the blank solution was mixed with a quantity of Ia-i nematicide and a small amount of BYK-016 antifoam agent in a 1 liter beaker. The formulation was then agitated with a Tekmar homogenizer at 9,000 rpm for 10 to 12 minutes, resulting in a slurry. The particle size of the pre-milled slurry was measured with a BECKMAN COULTER LS Particle Size Analyzer (model LS 13 320).

For formulation Sample A and Sample C the pre-milled slurry was then added to a NETZSCH MINI ZETA II apparatus filled with either glass or zirconium oxide beads (200 mL) equipped with cooling water. After milling for 35 minutes, the resulting white slurry was collected, and the particle size was measured as described above. Formulation Sample B was pre-milled only to give a median particle size of 5.8 μm. The particle size can be reduced further through optimization of the pre-milling process.

A stabilizer composition was prepared by adding KELZAN CC stabilizing agent (4.00 g) and PROXEL GXL biocide (8.00 g) to deionized water (388.00 g). After agitation with a mechanical stirrer at room temperature for 30 minutes, a homogeneous viscous liquid was obtained.

The milled slurry was then mixed with a stabilizer composition in a 9:1 weight ratio to provide a flowable suspension concentrate composition. A summary of three representative composition samples prepared according to this process is provided below:

TABLE 4

| Ingredient | Sample A (wt. %) | Sample B (wt. %) | Sample C (wt. %) |
|---|---|---|---|
| Ia-i | 45.91 | 45.91 | 45.91 |
| MORWET D-425 | 1.13 | 1.13 | 4.52 |
| Propylene glycol | 5.65 | 5.65 | 5.65 |
| Water | 35.99 | 35.99 | 32.60 |
| BYK-016 | 0.31 | 0.31 | 0.31 |
| PLURONIC ® L-35 | 0.06 | 0.06 | 0.06 |
| Buffer solution | 0.94 | 0.94 | 0.94 |
| Stabilizer (1% solution) | 10.00 | 10.00 | 10.00 |

As indicated above, the compositions prepared according to this process were all able to achieve an active ingredient loading of at least about 45% by weight. Each of the compositions was measured to have an average median particle size of from 1.0 to 1.2 microns, with a polydispersity index (median/mean) of from 1.4 to 1.5. Each of the compositions was observed to be storage stable at room temperature for more than three months.

The formulations can also be prepared with Netzch Mini Zeta II milling machine via a pass mode. In a typical example, the formulation was first pre-milled with a homogenizer and then added to the milling machine. After the formulation was passed through the milling machine, it was collected and then added to the milling machine again. After passing through the milling machine at 3504 rpm three times, the formulation was collected and mixed with the KELZAN stabilizer composition to give the final formulation. The particle size of the formulation was measured before the stabilizer was added. The formulations prepared by the multiple pass mode are shown in Table 5. The particle sizes for these formulations are shown in Table 6.

TABLE 5

| Ingredient | Sample D (wt. %) | Sample E (wt. %) | Sample F (wt. %) |
|---|---|---|---|
| Ia-i | 47.79 | 47.79 | 47.79 |
| MORWET D-425 | 2.26 | 2.26 | 2.26 |
| ISOPAR M | 2.26 | 2.26 | — |
| humic acid, sodium salt | 2.26 | — | 2.26 |
| Propylene glycol | 5.65 | 5.65 | 5.65 |
| Water | 39.06 | 41.32 | 41.32 |
| BYK-016 | 0.31 | 0.31 | 0.31 |
| PLURONIC ® L-35 | 0.06 | 0.06 | 0.06 |
| Buffer solution | 0.039 | 0.039 | 0.039 |
| Stabilizer composition | 0.10 | 0.10 | 0.10 |
| 1,2-benzisothiazolin-3-one | 0.20 | 0.20 | 0.20 |

TABLE 6

| Formulation | Mean (μm) | Median (μm) | Mean/Median |
|---|---|---|---|
| Sample D | 2.63 | 1.87 | 1.41 |
| Sample E | 2.80 | 1.93 | 1.45 |
| Sample F | 2.37 | 1.62 | 1.46 |

Example 11: Differential Scanning Calorimetry Analysis

Eleven batches of 3-phenyl-5-(thiophen-2-yl)-1,2,4-oxadiazole (Ia-i) were characterized for polymorphic form using differential scanning calorimetry (DSC) analysis. DSC data were collected using a TA INSTRUMENTS Q2000 DSC apparatus.

For each batch, samples in the mass range of 1 to 10 mg were crimped in aluminum sample pans and scanned over a range of 25° C. to about 120° C., increasing at a rate of 2° C. to 10° C. per minute, and using a nitrogen purge at 50 mL/min.

The melting point onset ranged from approximately 106° C. to 108° C., with enthalpy of fusion ranging from approximately 108 to 122 J/g. The results are shown below in Table 7. Enthalpy of fusion measurements were obtained on single sample analysis using a relatively small sample size of approximately 2 mg.

TABLE 7

DSC Analysis Summary

| Batch | Melting Point Onset | Enthalpy of Fusion (J/g) |
|---|---|---|
| A | 107.0 C. | 116.6 |
| B | 107.7 C. | 117.1 |
| C | 107.3 C. | 118.9 |
| D | 107.0 C. | 119.4 |
| E | 107.4 C. | 110.1 |
| F | 107.7 C. | 121.7 |
| G | 107.0 C. | 118.9 |
| H | 106.1 C. | 107.5 |
| I | 106.7 C. | 110.0 |
| J | 107.3 C. | 108.7 |
| K | 107.9 C. | 111.0 |

The thermal behavior of batch G was determined using differential scanning calorimetry and thermogravimetric analysis. The DSC thermogram exhibited a sharp melting endotherm with an onset of 106.9° C. and an enthalpy of fusion of 118.9 J/g.

Microscopic evaluation of lot G showed birefringent acicular to columnar shaped particles, ranging in size from approximately 5 to 100 microns. FIG. 1 shows the representative photomicrograph.

Example 12: Solvent Recrystallization

To perform the solvent-based portion of the polymorph screen, the 3-phenyl-5-(thiophen-2-yl)-1,2,4-oxadiazole test material was recrystallized using various solvents under approximately 240 different crystal growth conditions. The scale of the recrystallization experiments was from approximately 0.5 mL to 15 ml. The crystal growth conditions were changed by using binary gradient arrays of solvent mixtures and by changing the saturation temperature, growth temperature and evaporation rate (rate of supersaturation generation).

Saturated solutions were prepared by agitating excess (as possible) test material in contact with the various solvent systems at the saturation temperature. If solids did not completely dissolve in the solvent, the mother liquor was separated from the residual solids by filtration. The mother liquor was then heated above the saturation temperature (overheated) to dissolve any remaining solids. The temperature of each solution was then adjusted to the growth temperature and a controlled nitrogen shear flow was introduced to begin solvent evaporation.

The recrystallization conditions for the seven solvent based panels used during the study are summarized in Table 8A. Each recrystallization panel contained from 27 to 96 wells. The wells within each panel contained different solvent compositions. Because of the different solvent composition in each well, each well acted as a different crystal growth experiment. The compositional solvent matrices for the five recrystallization panels used during the solvent-based portion of the polymorph screen are shown below in Tables 8B through 8F, respectively. Based on the XRD analysis carried out on the screening samples (see Example 18, below) a new polymorph of 3-phenyl-5-(thiophen-2-yl)-1,2,4-oxadiazole was discovered in these experiments. The starting material was designated as Form I, while the new polymorph was designated as Form II.

TABLE 8A

Summary of Recrystallization Panels

| Panel | No. of Wells | Scale (mL) | Solvent | Saturation Temp. (° C.) | Overheat Temp. (° C.) | Growth Temp. (° C.) | N$_2$ Flow Rate (psi) |
|---|---|---|---|---|---|---|---|
| 1 | 34 | 15 | Single/Binary | 25 | 55 | 25 | 1.5 |
| 2 | 34 | 15 | Single/Binary | 25 | NA | 80 | 1.5 |
| 4 | 27 | 15 | Binary | 25 | 55 | 50 | 1.5 |
| 6 | 27 | 15 | Binary | 25 | NA | 65 | 1.5 |
| 7 | 96 | 0.5 | Binary | 25 | 50 | 40 | 2 |

TABLE 8B

Recrystallization Panel 1 (Evaporated at Room Temp)

| Well | Solvent | Sample ID | XRD Form |
|---|---|---|---|
| 1 | methanol | RC1-1 | Form I |
| 2 | ethanol | RC1-2 | Form I |
| 3 | trifluoroethanol | RC1-3 | Form I |
| 4 | 1-propanol | RC1-4 | Form I |
| 5 | 2-propanol | RC1-5 | Form I |
| 6 | 1-butanol | RC1-6 | Form I |
| 7 | 2-butanol | RC1-7 | Form I |
| 8 | water | RC1-8 | NA |
| 9 | dimethyl formamide | RC1-9 | Form I |
| 10 | dimethylacetamide | RC1-10 | Form I |
| 11 | butyl amine | RC1-11 | Form I |
| 12 | diisopropyl amine | RC1-12 | Form I |
| 13 | pyridine | RC1-13 | Form I |
| 14 | nitromethane | RC1-14 | Form I |
| 15 | acetone | RC1-15 | Form I |
| 16 | methyl ethyl ketone | RC1-16 | Form I |
| 17 | isopropyl ether | RC1-17 | Form I |
| 18 | Ethyl acetate | RC1-18 | Form I |
| 19 | methyl tert butyl ether | RC1-19 | Form I |
| 20 | isopropyl acetate | RC1-20 | Form I |
| 21 | tetrahydrofuran | RC1-21 | Form I |
| 22 | acetonitrile | RC1-22 | Form I |
| 23 | methylene chloride | RC1-23 | Form I |
| 24 | chloroform | RC1-24 | Form I |
| 25 | toluene | RC1-25 | Form I |
| 26 | heptane | RC1-26 | Form I |
| 27 | 1,4 dioxane | RC1-27 | Form I |
| 28 | NMP | RC1-28 | NA/T |
| 29 | DMSO | RC1-29 | NA/T |
| 30 | xylene | RC1-30 | Form I |
| 31 | butyl acetate | RC1-31 | Form I |
| 32 | 2-methyl tetrahydrofuran | RC1-32 | Form I |
| 33 | propylene glycol | RC1-33 | NA/T |
| 34 | glycerol/pyridine (2:13) | RC1-34 | NA/T |

TABLE 8C

Recrystallization Panel 2 (Evaporated at 80° C.)

| Well | Solvent | Sample ID | XRD Form |
|---|---|---|---|
| 1 | methanol | RC2-1 | Form I + II |
| 2 | ethanol | RC2-2 | Form I |
| 3 | trifluoroethanol | RC2-3 | Form I |
| 4 | 1-propanol | RC2-4 | Form I II |
| 5 | 2-propanol | RC2-5 | Form I |
| 6 | 1-butanol | RC2-6 | Form I |
| 7 | 2-butanol | RC2-7 | Form I + II |
| 8 | water/acetone (7.5/7.5) | RC2-8 | Form I |
| 9 | DMF/1-butanol (7.5/7.5) | RC2-9 | Form II |
| 10 | DMA/IPE (7.5/7.5) | RC2-10 | Form II |
| 11 | butyl amine | RC2-11 | Form I |
| 12 | diisopropyl amine | RC2-12 | Form I + II |
| 13 | pyridine | RC2-13 | Form I |
| 14 | nitromethane | RC2-14 | Form I + II |
| 15 | acetone | RC2-15 | Form I |
| 16 | methyl ethyl ketone | RC2-16 | Form II |
| 17 | isopropyl ether | RC2-17 | Form I |
| 18 | Ethyl acetate | RC2-18 | Form I + II |
| 19 | methyl tert butyl ether | RC2-19 | Form I |
| 20 | isopropyl acetate | RC2-20 | Form I + II |
| 21 | tetrahydrofuran | RC2-21 | Form I |
| 22 | acetonitrile | RC2-22 | Form I + II |
| 23 | methylene chloride | RC2-23 | Form I + II |
| 24 | chloroform | RC2-24 | Form I |
| 25 | toluene | RC2-25 | Form I + II |
| 26 | heptane | RC2-26 | Form I + II |
| 27 | 1,4 dioxane | RC2-27 | Form I + II |
| 28 | NMP/MeOH (7.5/7.5) | RC2-28 | Form II |
| 29 | DMSO/EtOH (7.5/7.5) | RC2-29 | Form I |
| 30 | xylene | RC2-30 | Form I |
| 31 | butyl acetate | RC2-31 | Form I + II |
| 32 | 2-methyl tetrahydrofuran | RC2-32 | Form I |
| 33 | PropGly/CHCl3 (7.5/7.5) | RC2-33 | Form I |
| 34 | glycerol/pyridine (1:14) | RC2-34 | Form I |

TABLE 8D

Recrystallization Panel 4 (Evaporated at 50° C.)
Solvent Matrix and XRD Result for Recrystallization Panel 4

| Solvent | Sample ID | Ratio of Solvents 1 | 2 | 3 | Co/Anti-Solvent |
|---|---|---|---|---|---|
| DMF | A | 12:3 | 7.5:7.5 | 3:12 | 1-butanol |
| DMA | B | 12:3 | 7.5:7.5 | 3:12 | IPE |
| MEK | C | 12:3 | 7.5:7.5 | 3:12 | EtOH |
| NMP | D | 12:3 | 7.5:7.5 | 3:12 | MeOH |
| TFE | E | 12:3 | 7.5:7.5 | 3:12 | Water |
| Xylene | F | 12:3 | 7.5:7.5 | 3:12 | IPA |
| EtOAc | G | 12:3 | 7.5:7.5 | 3:12 | 2-butanol |
| 1,4 dioxane | H | 12:3 | 7.5:7.5 | 3:12 | Heptane |
| DCM | I | 12:3 | 7.5:7.5 | 3:12 | Acetonitrile |

| Solvent | Sample ID | XRD Form 1 | 2 | 3 | Co/Anti-Solvent |
|---|---|---|---|---|---|
| DMF | A | Form I | Form I + II | Form I + II | 1-butanol |
| DMA | B | Form I | Form II | Form I + II | IPE |
| MEK | C | Form I + II | Form I | Form I | EtOH |
| NMP | D | Form II | Form I | Form I | MeOH |
| TFE | E | Form II | Form I | No sample | Water |
| Xylene | F | Form I | Form I | Form I | IPA |
| EtOAc | G | Form I | Form I | Form I | 2-butanol |
| 1,4 dioxane | H | Form I | Form I | Form I | Heptane |
| DCM | I | Form I | Form I | Form I | Acetonitrile |

TABLE 8E

Recrystallization Panel 6 (Evaporated at 65° C.)
Solvent Matrix and XRD Result for Recrystallization Panel 6

| Solvent | Sample ID | Ratio of Solvents 1 | 2 | 3 | Co/Anti-Solvent |
|---|---|---|---|---|---|
| TFE | A | 12:3 | 7.5:7.5 | 3:12 | Isopropyl Acetate |
| 1-propanol | B | 12:3 | 7.5:7.5 | 3:12 | MEK |
| THF | C | 12:3 | 7.5:7.5 | 3:12 | Chloroform |
| Butylamine | D | 12:3 | 7.5:7.5 | 3:12 | Toluene |
| Diisopropyl-amine | E | 12:3 | 7.5:7.5 | 3:12 | butyl acetate |
| Pyridine | F | 12:3 | 7.5:7.5 | 3:12 | 2-meth THF |
| Nitromethane | G | 12:3 | 7.5:7.5 | 3:12 | DMA |
| Acetone | H | 12:3 | 7.5:7.5 | 3:12 | NMP |
| MTBE | I | 12:3 | 7.5:7.5 | 3:12 | DMF |

| Solvent | Sample ID | XRD Form 1 | 2 | 3 | Co/Anti-Solvent |
|---|---|---|---|---|---|
| TFE | A | Form I + II | Form II | Form I + II | Isopropyl Acetate |
| 1-propanol | B | Form I + II | Form I + II | Form I | MEK |
| THF | C | Form I + II | Form I | Form I | Chloroform |
| Butylamine | D | Form I | Form I | Form I | Toluene |
| Diisopropyl-amine | E | Form I | Form I + II | Form I | butyl acetate |
| Pyridine | F | Form I + II | Form I | Form I | 2-meth THF |
| Nitromethane | G | Form I + II | Form I | Form I | DMA |
| Acetone | H | Form I + II | Form I | Amorphous/LC | NMP |
| MTBE | I | Form I | Form I | Form I | DMF |

TABLE 8F

Recrystallization Panel 7 (96 Well Plate, Evaporated at 40° C.)

| | | Pyridine 1 | Nitro-methane 2 | Acetone 3 | MEK 4 | EtOAc 5 | MTBE 6 | Isopropyl acetate 7 | THF 8 | DCM 9 | CHCl3 10 | Toluene 11 | 1,4 dioxane 12 |
|---|---|---|---|---|---|---|---|---|---|---|---|---|---|
| A | TFE | Form I | Form I | Form II | Form II | Form I | LC | NA | NA | Form I | NA | Form II | Form I |
| B | 1-propanol | NA | Form I + II | Form II | NA | Form I | Form I | Form I | NA | NA | LC | Form II | Form I |
| C | IPA | NA | Form II | Form II | NA | Form II | NA | Form I | NA | NA | NA | NA | NA |
| D | 2-butanol | LC | Form II | Form II | NA | Form I | NA | Form I | NA | NA | NA | NA | NA |
| E | DMF | NA | NA | NA | Form II | NA | NA | NA | Form I | Form II | NA | NA | NA |
| F | DMA | NA | NA | NA | NA | Form I | NA | NA | NA | NA | NA | Form I | NA |
| G | butyl-amine | NA | Form II | NA | NA | NA | Form I | NA | NA | Form I | NA | NA | NA |
| H | Di-isopropyl amine | Form II | Form I | Form I | NA | NA | NA | NA | NA | NA | NA | NA | NA |

Example 13: Recrystallization from the Melt

Cyclic DSC analysis was performed on lot G (Form I) to determine if 3-phenyl-5-(thiophen-2-yl)-1,2,4-oxadiazole would recrystallize from the melt as a different form (solvent-less recrystallization). Experiments were performed by heating the material above the melting temperature, then cooling the material at a rate of 5° C., 10° C., 20° C., 30° C., 40° C. or 50° C. per minute, followed by reheating above the melting temperature. At the 5° C. to 30° C. per minute cooling rates, the first enthalpy of fusion values (for the starting material) were approximately 120 J/g while the second values (for the melting of the solids obtained after cooling the original melt) were approximately 100 J/g. There was also a slight change in the melting point onset (approximately 0.5° C.). It is believed that melting Form I, followed by recrystallization, may result in the formation of Form II.

The results of the experiments performed at cooling rates of 40° C. and 50° C. per minute were unclear, and may indicate that the experiment was uncontrolled under these conditions.

Figure 3:
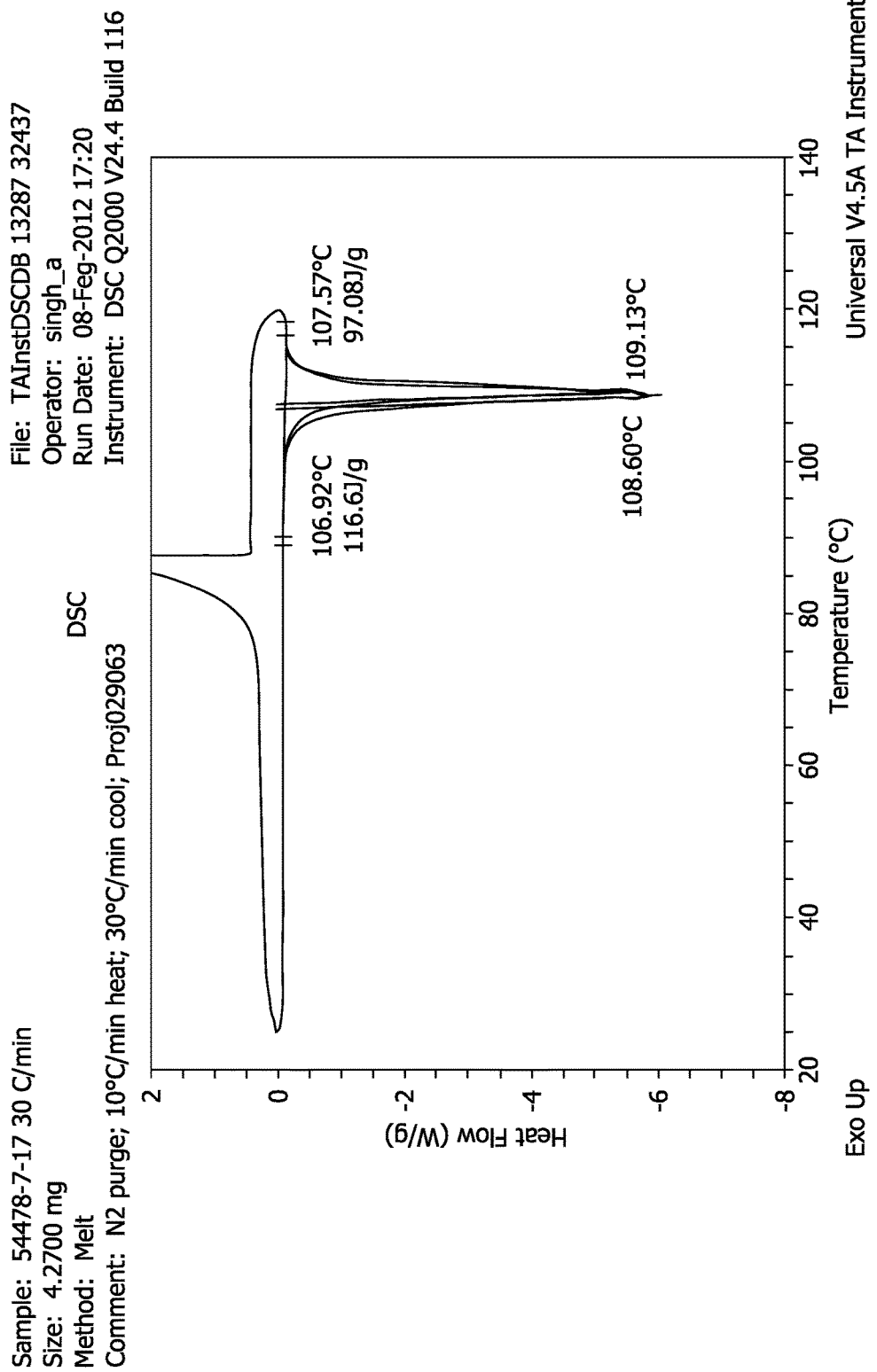
FIG. 3 depicts a sample cyclic differential scanning calorimetry (DSC) thermogram from a cyclic DSC analysis conducted on 3-phenyl-5-(thiophen-2-yl)-1,2,4-oxadiazole at a cooling rate of 30° C. per minute.

FIG. 3 shows a sample cyclic DSC thermogram from the run conducted at a cooling rate of 30° C. per minute.

In a further experiment, approximately 300-400 mg of Form I starting material was heated to melting in a forced air oven at approximately 120° C. for approximately 40 minutes. The sample was slow cooled to room temperature, and XRD, DSC and proton NMR analyses were performed on this sample. The XRD pattern was different from the starting material (Form I) and was similar to the Form II pattern. DSC exhibited a melting onset temperature of 107.8° C. and enthalpy of fusion of 103.2 J/g.

Example 14: Grinding Analysis

Batches of 3-phenyl-5-(thiophen-2-yl)-1,2,4-oxadiazole polymorphic Forms I and II were ground using a CRESCENT WIG-L-BUG ball mill for 2 minutes at 4800 oscillations per minute (3.2 m/s) in two separate experiments. Under these conditions, no transformation was observed in Form I, while the Form II sample transformed to Form I. FIG. 4 shows the XRD overlay of the milled Form I and Form II samples and the reference patterns of Forms I and II. The Form II used in this experiment was obtained by recrystallization from the melt of Form I, as described in Example 14, above,

Example 15: Mechanical Pressure Analysis

Figure 5A:
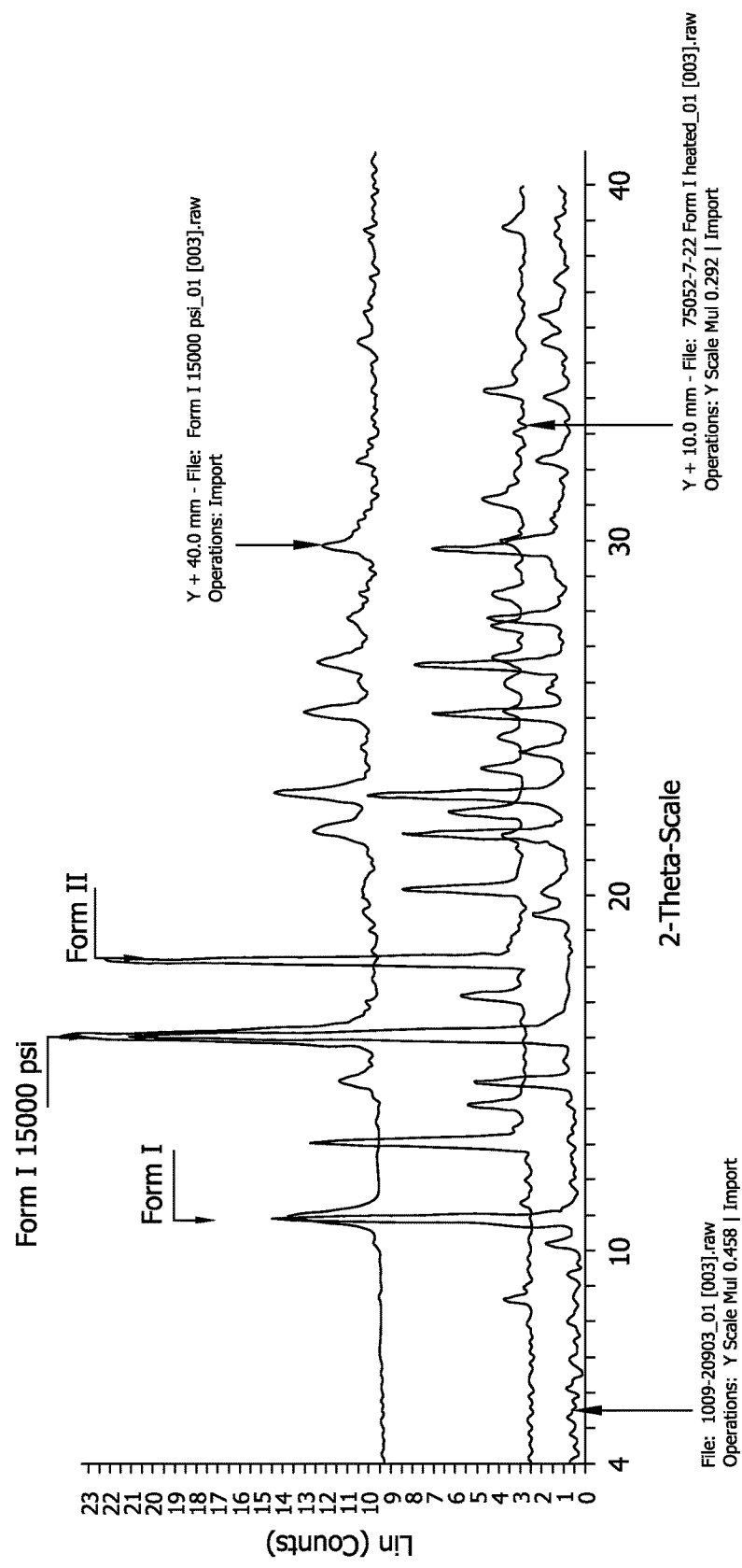
FIGS. 5A and 5B depict XRD overlay results for polymorphic Forms I and II of 3-phenyl-5-(thiophen-2-yl)-1,2,4-oxadiazole, respectively.
Figure 5B:
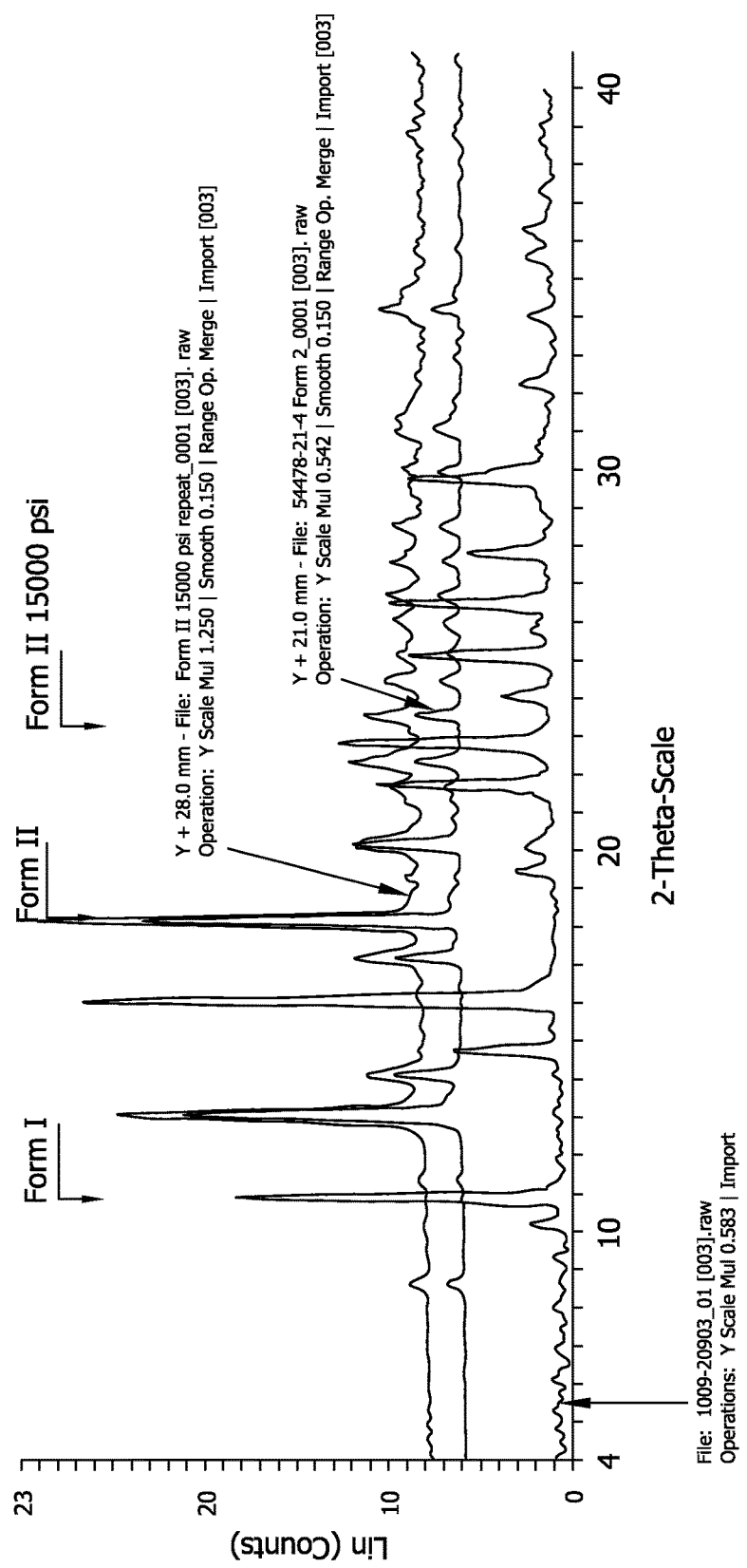

Batches of 3-phenyl-5-(thiophen-2-yl)-1,2,4-oxadiazole polymorphic Forms I and II were placed in a CARVER press and compressed at approximately 15,000 psi for approximately 20 seconds in two separate experiments. XRD analysis was performed on the samples. The resulting XRD pattern matched the starting material in both experiments, as shown in FIGS. 5A and 5B for Forms I and II, respectively. The pressurized treatment did not reveal any changes in the polymorphic form of the starting material in both experiments. The Form II used in this experiment was obtained by recrystallization from the melt of Form I, as described in Example 14, above.

Example 16: Non-Competitive Slurry Experiments

In addition to the solvent recrystallization experiments, non-competitive slurry experiments were performed to search for new solid-state forms of 3-phenyl-5-(thiophen-2-yl)-1,2,4-oxadiazole. These experiments rely on solubility differences of different polymorphic forms (if the compound exists in different polymorphic forms). As such, only polymorphs having a lower solubility (that is, are more stable) than the original crystalline form can result from a noncompetitive slurry experiment.

Essentially, when a solid is mixed with solvent to create slurry, a saturated solution eventually results. The solution is saturated with respect to the polymorphic form dissolved. However, the solution is supersaturated with respect to any polymorphic form that is more stable (more stable forms have lower solubility) than the polymorphic form initially dissolved. Therefore, any of the more stable polymorphic forms can nucleate and precipitate from solution. In addition, noncompetitive slurry experiments are often useful in identifying solvents that form solvates with the compound.

The slurry experiments were performed by exposing excess supplied material to solvents and agitating the resulting suspensions for several days at ambient temperature. The solids were filtered using a WHATMAN Grade 1 apparatus (11 μm pore size) and analyzed by XRD to determine the resulting form(s). To avoid possible desolvation or physical change after isolation, the samples were not dried before X-ray analysis. A summary of non-competitive slurry experiments is shown in Table 9.

TABLE 9

| Vehicle | Initial Form | Duration | Final Form |
|---|---|---|---|
| Methanol | I | 12 days | I |
| Ethanol | I | 12 days | I |
| Trifluoroethanol | I | 12 days | I |
| 1-propanol | I | 12 days | I |
| Isopropyl alcohol | I | 12 days | I |
| 1-butanol | I | 12 days | I |
| 2-butanol | I | 12 days | I |
| water | I | 12 days | I |
| heptane | I | 12 days | I |
| glycerol/water (1:10) | I | 12 days | I |
| propylene glycol/water (1:10) | I | 12 days | I |
| Isopropyl alcohol/water (1:1) | I | 12 days | I |
| ethanol | II | 7 days | I |
| trifluoroethanol | II | 7 days | I |
| 1-propanol | II | 7 days | I |
| Isopropyl alcohol | II | 7 days | I |
| 1-butanol | II | 7 days | I |
| 2-butanol | II | 7 days | I |
| heptane | II | 7 days | I |
| glycerol/water (1:10) | II | 7 days | I |
| propylene glycol/water (1:10) | II | 7 days | I |
| Isopropyl alcohol/water(1:1) | II | 7 days | I |

Based on their X-ray scattering behavior, the slurry experiments with Form I as the starting material resulted in Form I after approximately 12 days of slurring (indicating no transformation). The slurry experiments with Form II as the starting material (obtained by recrystallization from the melt, as set forth in Example 14, above) resulted in Form I after approximately 7 days of slurring. These data indicate that Form I is more stable than Form II at ambient temperature and pressure. No new polymorphs, solvates, or hydrates were isolated in these experiments.

Example 17: X-Ray Analysis of Screening Samples

Batches of solid 3-phenyl-5-(thiophen-2-yl)-1,2,4-oxadiazole polymorphs generated from the solvent based recrystallization panels and from other means (slurry, recrystallization from melt in an oven, etc.) were analyzed by powder XRD. To mitigate preferred grain effects, a two dimensional detection system was used to collect all the XRD screening data. The two dimensional detector integrates along the concentric Debye cones which helps reduce pattern variation. An example of the Debye cone integration using a two dimensional detector is shown below. If bright spots appear in the conical rings, it indicates strong preferred grain effects that can lead to considerable variability in the observed diffraction patterns including changes in peak intensities. Some samples of 3-phenyl-5-(thiophen-2-yl)-1,2,4-oxadiazole exhibited preferred grain effects based on the appearance of the scattering behavior.

Figure 7:
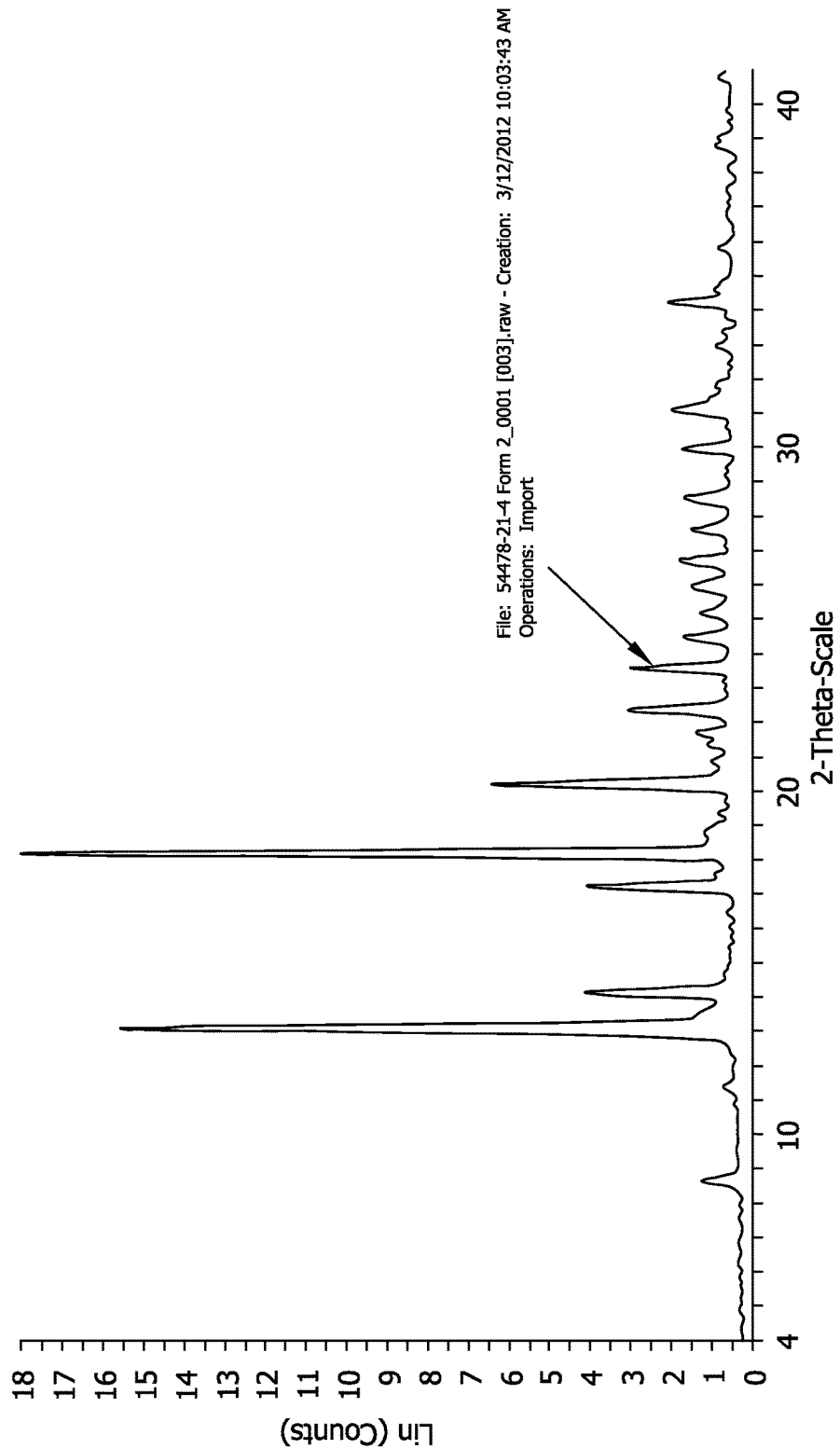
FIG. 7 depicts the results of a powder XRD analysis of the Form II polymorph of 3-phenyl-5-(thiophen-2-yl)-1,2,4-oxadiazole.

The results of this analysis revealed the material exists as two different polymorphs. The polymorphs were designated as Forms I and II. A powder XRD analysis of the Form I polymorphs, corresponding to the initial test samples, is set forth in FIG. 6. A powder XRD analysis of the Form II polymorphs is set forth in FIG. 7.

The initial test material was designated as Form I. The resulting form designation for each individual (solvent-based) recrystallization experiment is shown in Tables 7B through 7F, above.

Example 18: Summary of Formation of Forms I and II

A number of different crystallization conditions were used to produce the samples utilized in Examples 12 through 18, above. Polymorphic Form I of 3-phenyl-5-(thiophen-2-yl)-1,2,4-oxadiazole was obtained in approximately 50% of the experiments under various crystallization conditions. Polymorphic Form II was obtained in approximately 10% of the experiments also under various crystallization conditions. Mixtures of Forms I and II were obtained in approximately 11% of the experiments indicating that the two polymorphs have a tendency to nucleate and grow concomitantly. Form I appears to be the thermodynamically stable form under ambient conditions based on the results of the non competitive slurry experiment. The exact crystallization conditions are shown in Tables 7A through 7F, above.

Table 10 shows a summary of the results obtained in all the experiment panels in this study. Note that Panels 1, 2, 4, 6, and 7 are described in Example 13, above. Panel 3 corresponds to the recrystallization from the melt as set forth in Example 14, above. Panels 5 and 8 correspond to the noncompetitive slurry experiments conducted with respect to Form I and Form II, respectively, in Example 17, above.

TABLE 10

| Panel No. | No. of Experiments | Form I | Form II | Mix of Forms I and II | No Result |
|---|---|---|---|---|---|
| Panel 1 | 34 | 29 | 0 | 0 | 5 |
| Panel 2 | 34 | 17 | 4 | 13 | 0 |
| Panel 3 (Melt) | 5 | 0 | 3 | 0 | 2 |

TABLE 10-continued

| Panel No. | No. of Experiments | Form I | Form II | Mix of Forms I and II | No Result |
|---|---|---|---|---|---|
| Panel 4 | 27 | 19 | 3 | 4 | 1 |
| Panel 5 Form 1 NC Slurry | 12 | 12 | 0 | 0 | 0 |
| Panel 6 | 27 | 16 | 1 | 9 | 1 |
| Panel 7 96 well | 96 | 19 | 14 | 1 | 62 |
| Panel 8 Form 2 NC Slurry | 10 | 10 | 0 | 0 | 0 |
| Total | 245 | 122 | 25 | 27 | 71 |
| % of total | 100% | 50% | 10% | 11% | 29% |

Example 19: Competitive Slurry Experiments

In addition to the solvent recrystallization experiments, a competitive slurry experiment was also performed to determine the most stable polymorphic form of 3-phenyl-5-(thiophen-2-yl)-1,2,4-oxadiazole. These experiments rely on the solubility differences of different polymorphic forms. As such, only polymorphic forms (and solvates) having a lower solubility (more stable) than the form initially dissolved can result from a competitive slurry experiment.

Essentially, when a solid is dissolved in a (slurry) solvent, a saturated solution eventually results. The solution is saturated with respect to the polymorphic form dissolved. However, the solution is supersaturated with respect to any polymorphic form that is more stable (more stable forms have lower solubility) than the polymorphic form initially dissolved. Therefore, any of the more stable polymorphic forms can nucleate and precipitate from solution. In addition, competitive slurry experiments are often useful in identifying solvents that form solvates with the API.

The slurry experiment was performed by exposing excess material of Forms I and II to a small volume of neat solvent and agitating the resulting suspensions for several days at ambient temperature. The solids were filtered and analyzed by XRD to determine the resulting form. To avoid possible desolvation or physical change after isolation, the sample was not dried before x-ray analysis. Table 11 shows the results of the competitive slurry experiment.

TABLE 11

| Initial Forms (XRD) | Solvent | Slurry Duration | Final Form (XRD) |
|---|---|---|---|
| I & II | Isopropyl alcohol | 1 week | I |

The thermal data obtained above was used to calculate an approximate value for the transition temperature of conversion of Forms I and II using methods known in the art. The value obtained using this method was approximately 102° C. Based on these calculations, Form I is expected to be the stable form below this temperature and Form II above it. This is another characteristic of an enantiotropic polymorphic relationship.

Figure 8:
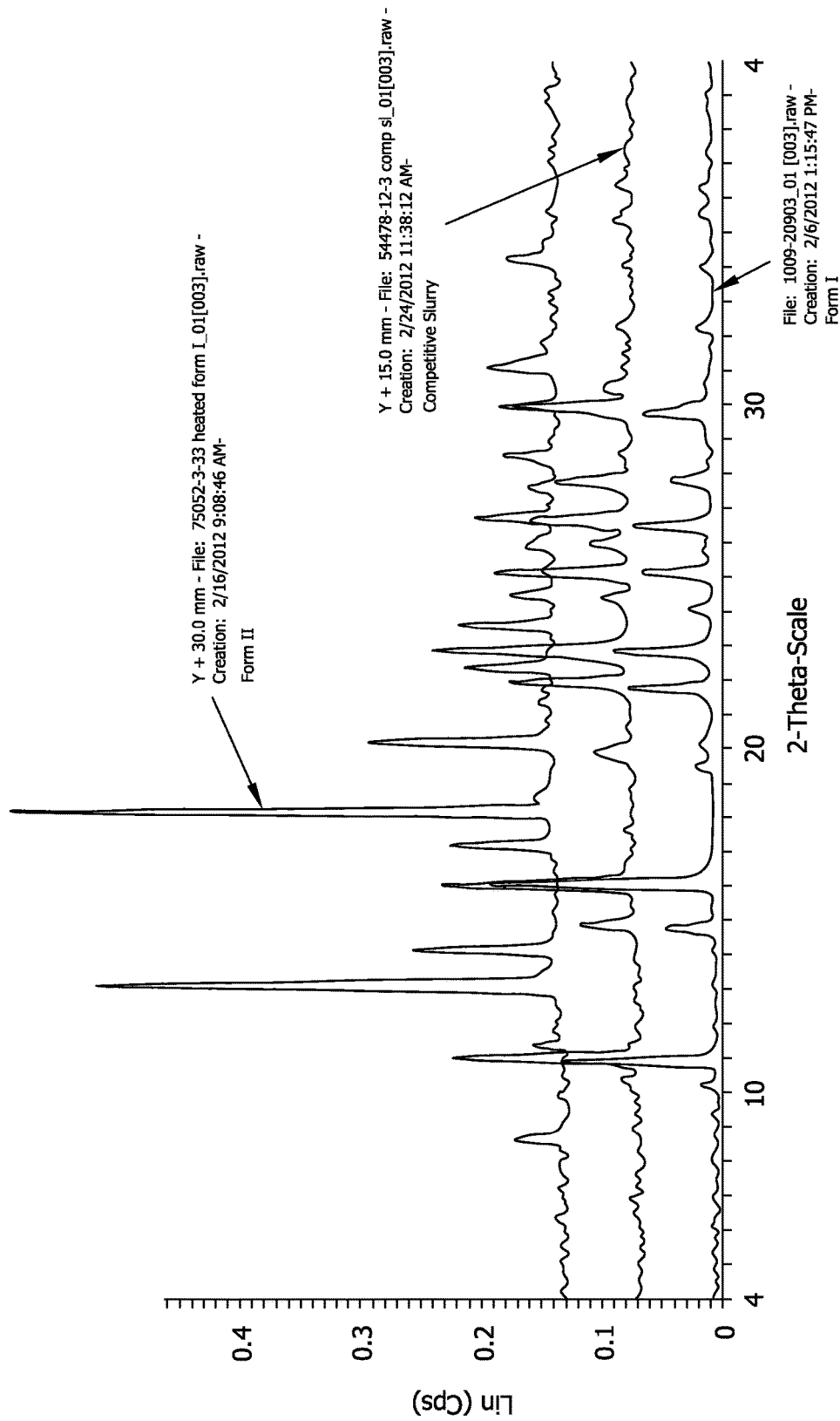
FIG. 8 depicts a graphical XRD overlay of the competitive slurry experiment between polymorphic Forms I and II of 3-phenyl-5-(thiophen-2-yl)-1,2,4-oxadiazole.

A graphical XRD overlay of the competitive slurry experiment is depicted in FIG. 8.

Example 20: Estimation of Transition Temperature

Figure 9A:
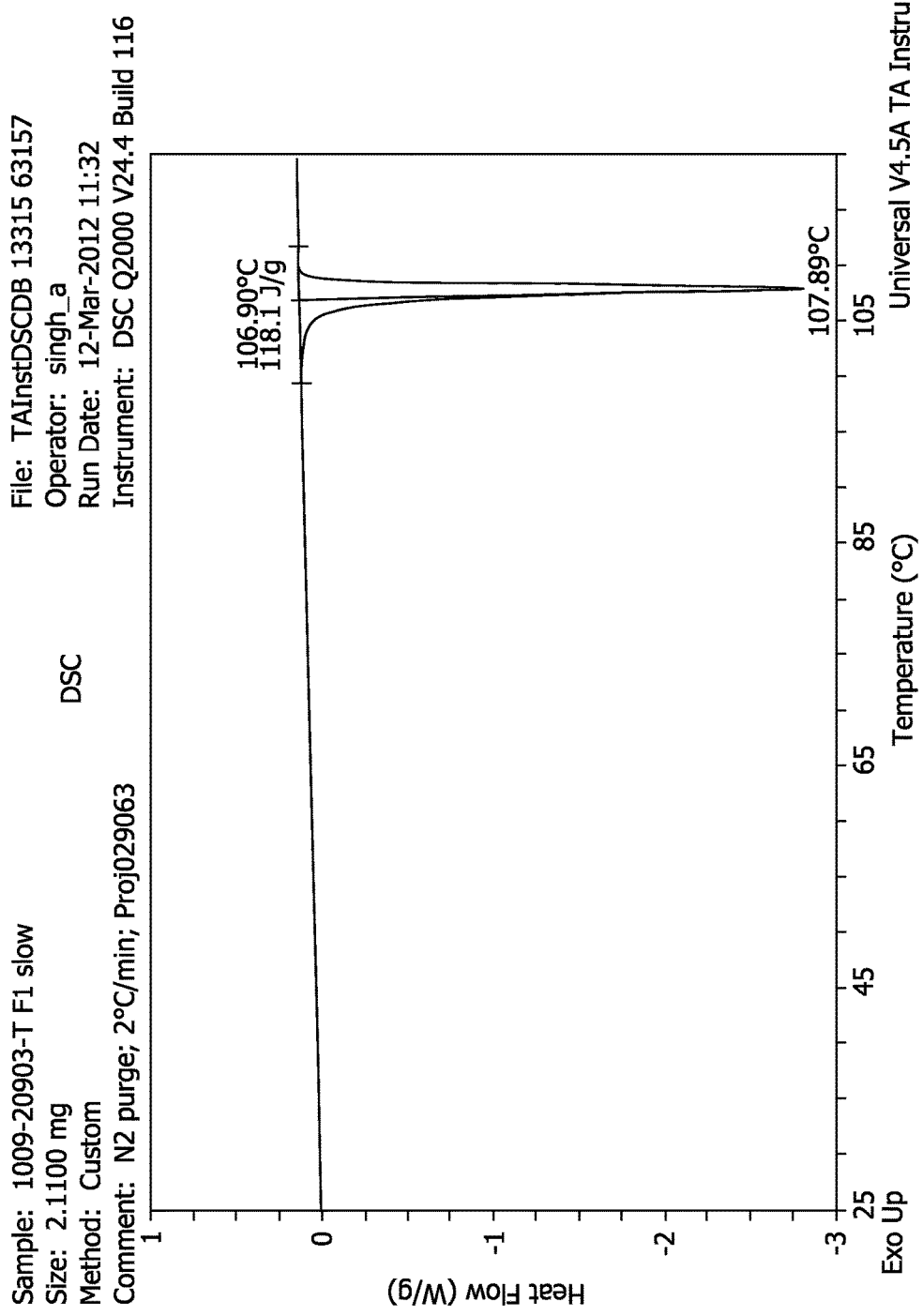
FIGS. 9A through 9C depict the relevant DSC thermograms for polymorphic Form I, polymorphic Form II, and a mixture of polymorphic Forms I and II, respectively, of 3-phenyl-5-(thiophen-2-yl)-1,2,4-oxadiazole.
Figure 9B:
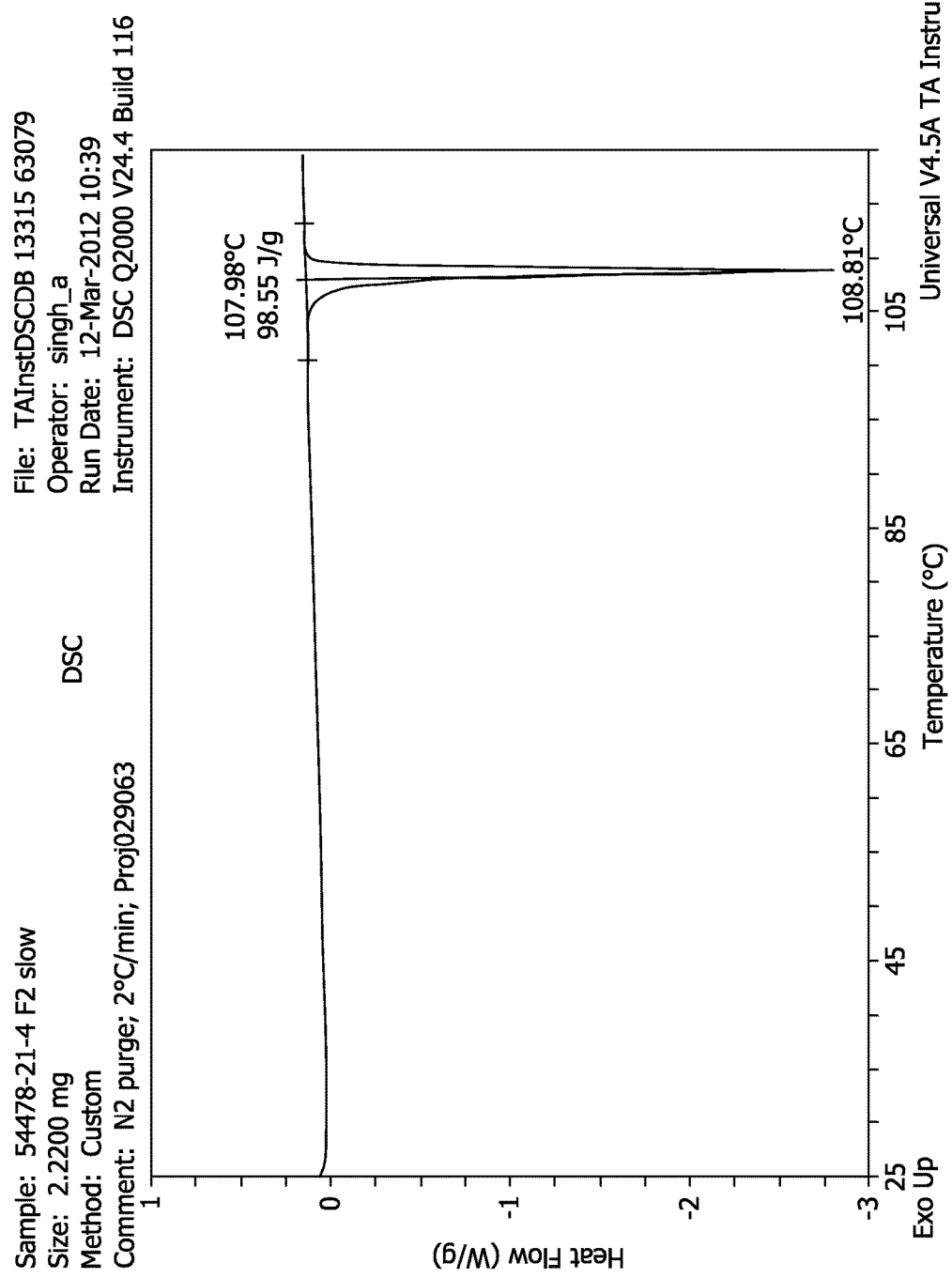
Figure 9C:
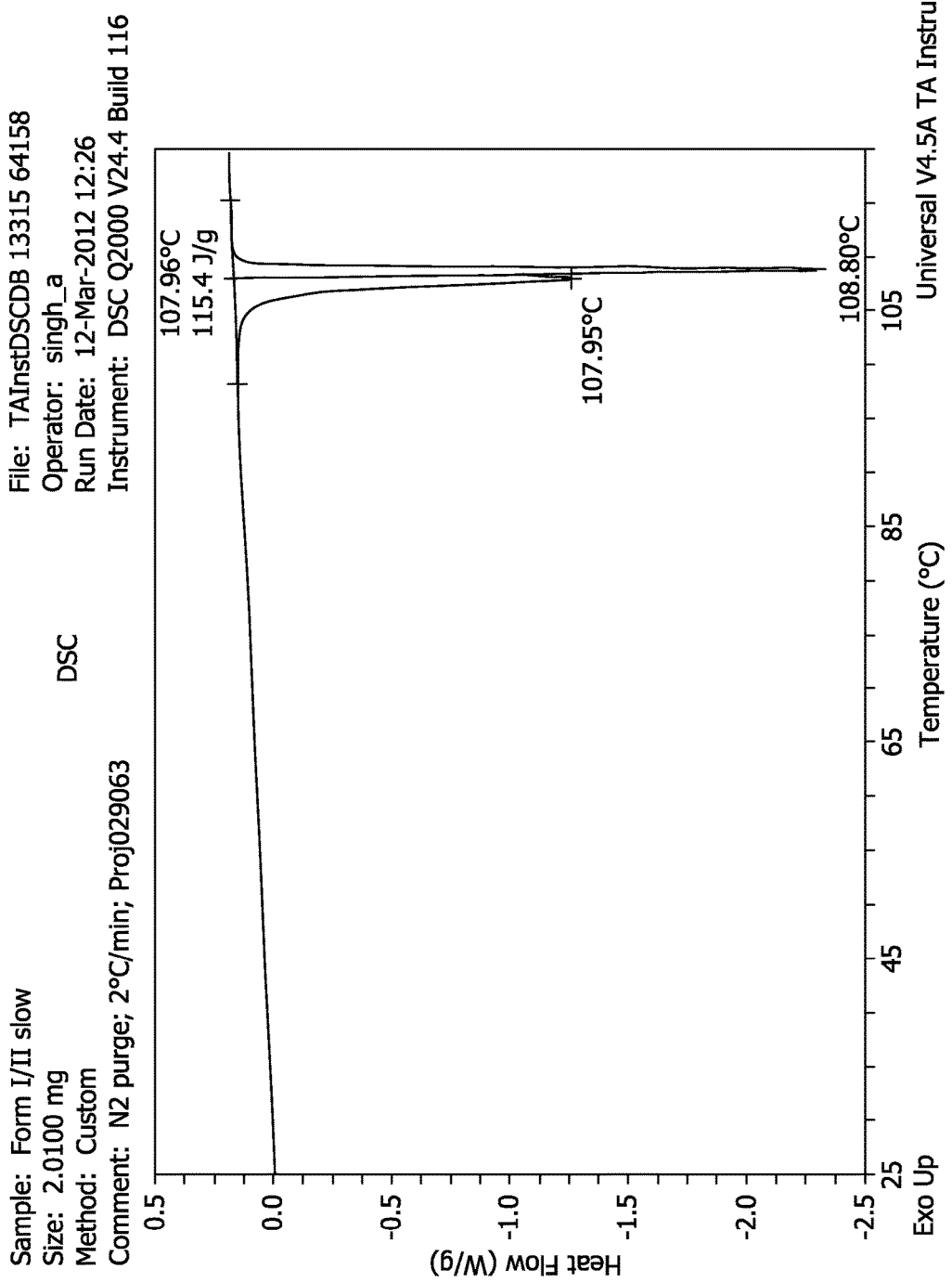

Polymorphic Forms I and II of 3-phenyl-5-(thiophen-2-yl)-1,2,4-oxadiazole, as well as a 50/50 mixture thereof, were analyzed by DSC at a slow heating rate of 2° C. per minute, with similar sample sizes. The melting temperatures and enthalpy of fusion data are shown in Table 12, below. These data indicate that Form I has a lower melting temperature and a higher enthalpy of fusion. Form II has a higher melting temperature and a lower enthalpy of fusion. In accordance with the Heat of Fusion Rule, this indicates that Form I and II have an enantiotropic relationship. FIGS. 9A through 9C show the relevant DSC thermograms for Form I, Form II, and a mixture of Forms I and II, respectively.

The thermal data using the procedure set forth above was used to calculate an approximate value for the transition temperature of conversion of Forms I and II, resulting in an estimated transition temperature value of 102° C. Based on these calculations, Form I is expected to be the stable form below this temperature, while Form II is expected to possess greater thermodynamic stability above that temperature. This further indicates that Forms I and II exhibit an enantiotropic polymorphic relationship.

TABLE 12

| Sample ID | Onset (° C.) | Maximum (° C.) | Enthalpy of Fusion (J/g) |
|---|---|---|---|
| Batch G Form I | 106.9 | 107.9 | 117.9 |
| 54478-21-4 Form II | 108.0 | 108.8 | 98.3 |
| 50/50, Form I/II | 108.0 | 108.0, 108.8 | 114.6 |

Example 21: Storage Stability of Polymorphs

To determine the storage stability and/or hydrate formation of 3-phenyl-5-(thiophen-2-yl)-1,2,4-oxadiazole Form I material during storage at ambient conditions, samples were monitored in two static humidity chambers. In these studies, samples were stored in open Petri dishes in chambers containing saturated salt solutions to maintain the relative vapor pressure. Solutions of saturated potassium chloride (84% RH) and sodium chloride (75% RH) salts at ambient temperature were used.

FIG. 10 shows the XRD pattern of the samples stored at 75 and 84% RH after 4 weeks of storage. As indicated in the figure, Form I does not form a hydrate and appears to be thermodynamically stable over time at ambient conditions.

In contrast, samples of Form II stored in a scintillation vial in a hood under ambient conditions showed signs of transformation to Form I when analyzed by XRD after approximately 6 days of storage. FIG. 11 shows the XRD overlays of Forms I, II and the sample of Form II which showed signs of transformation to Form I.

Example 22: Soybean Cyst Nematode Assay

Formulations were tested for nematicidal activity against soybean cyst nematode (SCN) in an SCN cup assay.

The formulations were prepared as follows:

Preparation of the phosphate buffer solution: To a 1 L volumetric flask were added potassium phosphate monobasic anhydrous (9.329 g) and sodium phosphate dibasic heptahydrate (32.756 g). DI water was added to the flask to the mark and it was inverted 15 times to give a clear solution.

Preparation of Formulation Blank A:

To a 2 L beaker were added MORWET D-425 (43.6 g), DI water (1,386.9 g), the phosphate buffer solution (36.3 g), propylene glycol (217.7 g), and PLURONIC L-35 (2.2 g). The mixture was stirred with a spatula to give a brown solution.

Preparation of Formulation Blank B:

To a 2 L beaker were added MORWET D-425 (174.3 g), DI water (1.256.0 g), the phosphate buffer solution (36.3 g), propylene glycol (217.8 g), and PLURONIC L-35 (2.1 g). The mixture was stirred with a spatula to give a dark brown solution.

Preparation of the KELZAN Stabilizer Solution:

To a 1 L beaker were added KELZAN CC (4.060 g), PROXEL GXL (7.978 g), and DI water (388.273 g). The mixture was then agitated with a Melton mechanical stirrer (model CM-100) at 2,000 rpm for 30 minutes to give a viscous liquid.

Preparation of Suspension Concentrate Formulation 3:

To a 2 L beaker were added Formulation Blank A (497.3 g), Compound Ia-i (521.4 g), and BYK-016 (3.6 g). The mixture was stirred with a spatula to give a slurry. The mixture was placed in an ice bath and a Tekmar T554 homogenizer (model TR-10) was used for the pre-milling. During the pre-milling, the slurry (1022.3 g) was agitated with the homogenizer at 9,000 rpm for 12 mins. An Eiger mill (model M250) was filled with zirconium oxide beads with an average diameter of 0.3-0.4 mm. Nearly half of the pre-milled slurry (501.4 g) was then added to the Eiger mill and was milled with a speed of 5000 rpm in recycle mode at room temperature. After 30 minutes, the resulting white liquid formulation (412.4 g) was collected and mixed with the KELZAN stabilizer solution (45.8 g) to give the final formulation (458.2 g). The particle size of the formulation was analyzed with a Beckman Coulter particle size analyzer (Model LS 13 320) before the stabilizer was added.

Preparation of Suspension Concentrate Formulation 4:

The pre-milled slurry (501.4 g) from the suspension concentrate formulation above was also milled with the same Eiger mill filled with zirconium oxide beads with an average diameter of 0.3-0.4 mm. After milling for 120 minutes, the resulting white liquid formulation (408.5 g) was collected and mixed with the KELZAN stabilizer solution (45.4 g) to give the final formulation (453.9 g). The particle size of the formulation was also analyzed with a Beckman Coulter particle size analyzer (Model LS 13 320) before the stabilizer was added.

Preparation of Suspension Concentrate Formulation 5:

To a 1 L beaker were added Formulation Blank B (383.3 g), Compound Ia-i (261.1 g), and BYK-016 (2.5 g). The mixture was stirred with a spatula to give a slurry. The mixture was placed in an ice bath and a Tekmar T554 homogenizer (model TR-10) was used for the pre-milling. During the pre-milling, the slurry was agitated with the homogenizer at 9,000 rpm for 10 mins. The milling was divided into two stages. Both Netzsch Mini Zeta II filled with glass beads with an average diameter of 0.8-1 mm and Eiger mill (model M250) filled with zirconium oxide beads with an average diameter of 0.1-0.2 mm were used in the milling. In the first stage, the slurry was passed through the Netzsch miller three times and the miller was operated at 3,504 rpm for each pass. In the second stage, the slurry was passed through the Eiger miller ten times and the milling was operated at 5,000 rpm. A white liquid (452.1 g) was collected and part of the white liquid (349.0 g) mixed with the KELZAN stabilizer solution (38.8 g) to give the final formulation (387.8 g). The particle size of the formulation was also analyzed with a Beckman Coulter particle size analyzer (Model LS 13 320) before the stabilizer was added.

Preparation of Suspension Concentrate Formulation 6:

To an 8 dram vial were added MORWET D-425 (0.714 g), DI water (3.75 g), the phosphate buffer solution (0.147 g), ISOPAR M (1.45 g), propylene glycol (0.898 g), PLURONIC L-35 (0.009 g), Compound Ia-i (7.315 g), and BYK-016 (0.067 g). The mixture was stirred followed by addition of 3 mm diameter stainless steel beads (14 mL). The vial was capped and placed on a US Stoneware roller (Ser. No. CK-11009) and rotated at a speed setting of 50. After 2 days the slurry (5.903 g) was collected and mixed with the KELZAN stabilizer solution (0.660 g) to give the final formulation (6.563 g). The particle size of the formulation was analyzed with a Beckman Coulter particle size analyzer (Model LS 13 320) before the stabilizer was added.

Table 13 below depicts the compositions of each formulation used for seed treatment in the SCN efficacy assay.

TABLE 13

| Treatment | Formulation Ia-i | Ia-i Formulation (g) | Commercial Seed Treatment (g) | Water (g) | Compound Ia-i Rate (mg/seed) |
|---|---|---|---|---|---|
| 1 | NA | N/A | N/A | N/A | N/A |
| 2 | NA | 0 | 1.557 | 0.64 | N/A |
| 3A | 3 | 0.36 | 0 | 0.64 | 0.05 |
| 3B | 3 | 2.16 | 0 | 1.01 | 0.3 |
| 4A | 3 | 0.36 | 1.557 | 0.64 | 0.05 |
| 4B | 3 | 2.16 | 1.557 | 1.01 | 0.3 |
| 5A | 4 | 0.36 | 0 | 0.64 | 0.05 |
| 5B | 4 | 2.16 | 0 | 1.01 | 0.3 |
| 6A | 4 | 0.36 | 1.557 | 0.64 | 0.05 |
| 6B | 4 | 2.16 | 1.557 | 1.01 | 0.3 |
| 7A | 5 | 0.45 | 0 | 1.21 | 0.05 |
| 7B | 5 | 2.73 | 0 | 1.16 | 0.3 |
| 8A | 5 | 0.45 | 1.557 | 1.21 | 0.05 |
| 8B | 5 | 2.73 | 1.557 | 1.16 | 0.3 |
| 9A | 6 | 0.36 | 0 | 0.64 | 0.05 |
| 9B | 6 | 2.16 | 0 | 1.01 | 0.3 |
| 10A | 6 | 0.36 | 1.557 | 0.64 | 0.05 |
| 10B | 6 | 2.16 | 1.557 | 1.01 | 0.3 |

SCN Efficacy Assay

A4630 soybean plants were grown in cups filled with full strength Murashige & Skoog basal salts fertilizer (Phytotech Cat. No. 201080-52) followed by 180 ml of 20:80 soil/sand mixture (sterile St. Charles sand and US 10 soil premixed by Hummert). A Gustafson Batch Modular Coater (BMC) Treater was used to the treat the soybean seeds with the formulations as described in Table 13.

The untreated seed and treated seed were placed on top of 20:80 soil and pushed ½ inch deep into the soil. The cups were placed in the growth chamber and the soil was misted with water to saturation. Propagation domes were placed over the cups until the seeds had germinated (about 3 to 5 days). Conditions in the growth chamber were as follows: 28° C., 60% relative humidity, and 16 h/14 h day/night periods, with 347µ Einsteins of light.

Ten days after planting, soybean cyst inoculum (2×500 µL, 5000 eggs/cup) was delivered into the soil on two sides of the soybean plant. The plants were grown for an additional 5 weeks after inoculation and watered as needed with overhead watering.

The efficacy of the formulations was determined by harvesting plants (45 days) and counting cysts. Table 14 summarizes the bioefficacy against SCN at 50 µg/seed and 300 µg/seed.

TABLE 14

| Treatment | Particle Size (μm) | Rate (mg/seed) | Cyst Counts Mean | Std Dev | Std Err Mean |
|---|---|---|---|---|---|
| 1 | N/A | | 227 | 159 | 65 |
| 2 | N/A | | 337 | 205 | 84 |
| 3A | 0.8 | 0.05 | 149 | 80 | 33 |
| 3B | | 0.3 | 67 | 47 | 19 |
| 4A | 0.8 | 0.05 | 247 | 244 | 100 |
| 4B | | 0.3 | 92 | 106 | 43 |
| 5A | 0.48 | 0.05 | 146 | 55 | 22 |
| 5B | | 0.3 | 90 | 58 | 24 |
| 6A | 0.48 | 0.05 | 203 | 193 | 79 |
| 6B | | 0.3 | 57 | 71 | 29 |
| 7A | 0.065 | 0.05 | 137 | 86 | 35 |
| 7B | | 0.3 | 150 | 55 | 25 |
| 8A | 0.065 | 0.05 | 176 | 101 | 41 |
| 8B | | 0.3 | 86 | 70 | 29 |
| 9A | 1.7 | 0.05 | 147 | 97 | 40 |
| 9B | | 0.3 | 80 | 89 | 36 |
| 10A | 1.7 | 0.05 | 92 | 63 | 28 |
| 10B | | 0.3 | 76 | 64 | 26 |

Example 23: Preparation of Suspension Concentrates Comprising 3-phenyl-5-(thiophen-2-yl)-1,2,4-oxadiazole (Ia-i) and imidacloprid Several suspension concentrate co-formulation compositions comprising the nematicidal compound 3-phenyl-5-(thiophen-2-yl)-1,2,4-oxadiazole (Ia-i) and imidacloprid were prepared. A summary of five representative co-formulation compositions prepared in this Example is provided below in Tables 15-19.

The phosphate buffer was prepared by adding potassium phosphate monobasic anhydrous (9.361 g) and sodium phosphate dibasic heptahydrate (32.732 g) to a 1 L volumetric flask. Then DI water was added to the flask to the mark. After it was shaken for a while, all the salts were dissolved to give a clear phosphate buffer with pH at 7.

The KELZAN thickener/stabilizer was prepared by adding KELZAN CC (4.00 g) and PROXEL GXL (8.00 g) to DI water (388.00 g) and agitating with a mechanical disperser at 2,900 rpm at room temperature for 30 minutes to obtain a viscous liquid (400 g).

The suspension concentrate co-formulation compositions were prepared by mixing all the ingredients in Part A at 300 rpm for 30 minutes or until the MORWET D-425 dissolved; adding all the ingredients in Part B to Part A and mixing at 300 rpm for 5 minutes; adding all the ingredients in Part C to the mixture of Parts A and B and homogenizing the solution at 9,000 rpm for 10 minutes; preparing a combination of ground (grinding was done using the roller with grinding media (Very High Density Zirconium Oxide Grinding Media, Yttria stabilized ½×½ cylinders)) Ia-i and imidacloprid (Part D) in a jar and pouring the solution above (Parts A, B, and C) in a controlled path; homogenizing the solution at 9000 rpm for 30 minutes with an ice bath; milling the solution 4 times to achieve the desired particle size; adding Part E to the collected sample and mixing at 500 rpm for 10 minutes; and adding Parts F, G and H (if present) to the collected sample and mixing at 900 rpm for 30 minutes.

ATLOX 4913 (available from Croda) is used as a crystal growth inhibitor. The weight percentage values reported in Tables 15-19 are theoretical, and were calculated based upon the weight of the actives added. Particle sizes reported in Tables 15-19 were measured by Beckman Coulter particle size analyzer (Beckman Coulter LS 13 320 laser diffraction particle size analyzer).

TABLE 15

Co-Formulation of Ia-i and Imidacloprid (particle size 2.196 μm)

| Part | Ingredient | Amount (g) | Theoretical Wt % | Actual Wt % |
|---|---|---|---|---|
| A | MORWET D-425 | 0.36 | 2.17 | |
| | DI water | 2.45 | 14.78 | |
| B | Buffer | 0.15 | 0.90 | |
| | DI water | 2.44 | 14.72 | |
| C | Propylene glycol | 0.90 | 5.43 | |
| | ISOPAR M | 0.36 | 2.17 | |
| | Antifoam | 0.05 | 0.30 | |
| | PLURONIC L-35 | 0.009 | 0.05 | |
| D | Ia-i | 5.93 | 35.77 | 34.1 |
| | Imidacloprid | 1.68 | 10.13 | 8.7 |
| E | Stabilizer | 1.59 | 9.60 | |
| | Humic acid sodium salt | 0.66 | 3.98 | |

TABLE 16

Co-Formulation of Ia-i and Imidacloprid (particle size 1.91 μm)

| Part | Ingredient | Amount (g) | Theoretical Wt % | Actual Wt % |
|---|---|---|---|---|
| A | MORWET D-425 | 0.36 | 2.17 | |
| | DI water | 2.45 | 14.74 | |
| B | Buffer | 0.15 | 0.90 | |
| | DI water | 2.44 | 14.68 | |
| C | Propylene glycol | 0.90 | 5.42 | |
| | ISOPAR M | 0.36 | 2.17 | |
| | Antifoam | 0.05 | 0.30 | |
| | PLURONIC L-35 | 0.009 | 0.05 | |
| D | Ia-i | 5.17 | 31.11 | 28.97 |
| | Imidacloprid | 2.44 | 14.68 | 13.17 |
| E | ATLOX 4913 | 0.34 | 2.05 | |
| F | Stabilizer | 1.59 | 9.58 | |
| G | Humic acid sodium salt | 0.36 | 2.17 | |

TABLE 17

Co-Formulation of Ia-i and Imidacloprid (particle size 1.95 μm)

| Part | Ingredient | Amount (g) | Theoretical Wt % | Actual Wt % |
|---|---|---|---|---|
| A | MORWET D-425 | 0.36 | 2.17 | |
| | DI water | 2.45 | 14.74 | |
| B | Buffer | 0.15 | 0.90 | |
| | DI water | 2.44 | 14.68 | |
| C | Propylene glycol | 0.90 | 5.42 | |
| | ISOPAR M | 0.36 | 2.17 | |
| | Antifoam | 0.05 | 0.30 | |
| | PLURONIC L-35 | 0.009 | 0.05 | |
| D | Ia-i | 5.17 | 31.11 | 28.82 |
| | Imidacloprid | 2.44 | 14.68 | 12.97 |
| E | ATLOX 4913 | 0 | 0 | |
| F | Stabilizer | 1.59 | 9.58 | |
| G | Humic acid sodium salt | 0 | 0.00 | |
| H | Water | 0.7 | 4.21 | |

TABLE 18

Co-Formulation of Ia-i and Imidacloprid (particle size 1.94 μm)

| Part | Ingredient | Amount (g) | Theoretical Wt % | Actual Wt % |
|---|---|---|---|---|
| A | MORWET D-425 | 0.36 | 2.17 | |
| | DI water | 2.45 | 14.74 | |
| B | Buffer | 0.15 | 0.90 | |
| | DI water | 2.44 | 14.68 | |

TABLE 18-continued

Co-Formulation of Ia-i and Imidacloprid (particle size 1.94 μm)

| Part | Ingredient | Amount (g) | Theoretical Wt % | Actual Wt % |
|---|---|---|---|---|
| C | Propylene glycol | 0.90 | 5.42 | |
|  | ISOPAR M | 0.36 | 2.17 | |
|  | Antifoam | 0.05 | 0.30 | |
|  | PLURONIC L-35 | 0.009 | 0.05 | |
| D | Ia-i | 5.17 | 31.11 | 29.11 |
|  | Imidacloprid | 2.44 | 14.68 | 13.19 |
| E | ATLOX 4913 | 0 | 0 | |
| F | Stabilizer | 1.59 | 9.58 | |
| G | Humic acid sodium salt | 0.36 | 2.17 | |
| H | Water | 0.34 | 2.05 | |

TABLE 19

Co-Formulation of Ia-i and Imidacloprid (particle size 1.92 μm)

| Part | Ingredient | Amount (g) | Theoretical Wt % | Actual Wt % |
|---|---|---|---|---|
| A | MORWET D-425 | 0.36 | 2.17 | |
|  | DI water | 2.45 | 14.74 | |
| B | Buffer | 0.15 | 0.90 | |
|  | DI water | 2.44 | 14.68 | |
| C | Propylene glycol | 0.90 | 5.42 | |
|  | ISOPAR M | 0.36 | 2.17 | |
|  | Antifoam | 0.05 | 0.30 | |
|  | PLURONIC L-35 | 0.009 | 0.05 | |
| D | Ia-i | 5.17 | 31.11 | 28.95 |
|  | Imidacloprid | 2.44 | 14.68 | 13.36 |
| E | ATLOX 4913 | 0.34 | 2.05 | |
| F | Stabilizer | 1.59 | 9.58 | |
| G | Humic acid sodium salt | 0 | 0.00 | |
| H | Water | 0.36 | 2.17 | |

Example 24: Aged Stability Studies of Suspension Concentrates Comprising 3-phenyl-5-(thiophen-2-yl)-1,2,4-oxadiazole (Ia-i) and imidacloprid The five suspension concentrate co-formulation compositions comprising the nematicidal compound 3-phenyl-5-(thiophen-2-yl)-1,2,4-oxadiazole (Ia-i) and imidacloprid prepared in Example 23 were subjected to an aged stability study.

In this study, particle size was measured by Beckman Coulter particle size analyzer (Beckman Coulter LS 13 320 laser diffraction particle size analyzer), viscosity was measured by Brookfield R/S plus Rheometer, and the wt % values of Ia-i and imidacloprid were determined using HPLC.

Each concentrate co-formulation composition was sampled into individual jars and labeled for room temperature (RT) time 0, RT 4 weeks, RT 8 weeks, 50° C. 4 weeks and 50° C. 8 weeks. Both 50° C. 4 weeks and 50° C. 8 weeks samples were stored in a lab oven with temperature set at 50° C.

At time 0, RT time 0 samples were tested. At 4 weeks, the 50° C. 4 weeks samples were taken out of oven and set on the bench for 24 hours to let the temperature reach RT. Then the RT 4 weeks samples and 50° C. 4 weeks samples were tested. At 8 weeks, the 50° C. 8 weeks samples were taken out of oven and set on the bench for 24 hours to let the temperature reach RT. Then the RT 8 weeks samples and 50° C. 8 weeks samples were tested.

The testing results of the aged stability study for the five suspension concentrate co-formulation compositions summarized in Tables 15-19 are reported below in Tables 20-24, respectively. Note that there is a slight discrepancy in the measured concentrations of Ia-i and imidacloprid as compared to the theoretical values reported above in Tables 15-19 for reasons known in the art; for example, the actives may not have been 100% pure, or there may have been loss of active during the milling and/or processing of the sample.

TABLE 20

Aged Stability Studies for Composition in Table 15

| | Time | | | | |
|---|---|---|---|---|---|
| | 0 | 4 weeks (RT) | 4 weeks (50° C.) | 8 weeks (RT) | 8 weeks (50° C.) |
| Concentration Ia-i (wt %) | 34.1 | 34.3 | 34.2 | 33.8 | 33.7 |
| Concentration imidacloprid (wt %) | 8.7 | 8.88 | 9.08 | 8.8 | 8.6 |
| Particle size (μm) | 2.196 | 1.949 | 2.061 | 2.094 | 1.927 |
| Viscosity (cP) | 134.68 | 185.35 | 212.85 | 164.97 | 202.32 |
| pH | 9.28 | 9.25 | 9.09 | 9.32 | 8.91 |

TABLE 21

Aged Stability Studies for Composition in Table 16

| | Time | | | | |
|---|---|---|---|---|---|
| | 0 | 4 weeks (RT) | 4 weeks (50° C.) | 8 weeks (RT) | 8 weeks (50° C.) |
| Concentration Ia-i (wt %) | 28.97 | 29.43 | 29.43 | 30.13 | 30.12 |
| Concentration imidacloprid (wt %) | 13.17 | 14.45 | 14.42 | 13.9 | 13.86 |
| Particle size (μm) | 1.913 | 1.97 | 1.972 | 1.86 | 1.904 |
| Viscosity (cP) | 92.46 | 101.54 | 123.32 | 99.82 | 119.71 |
| pH | 9.09 | 8.91 | 8.44 | 8.83 | 8.55 |

TABLE 22

Aged Stability Studies for Composition in Table 17

| | Time | | | | |
|---|---|---|---|---|---|
| | 0 | 4 weeks (RT) | 4 weeks (50° C.) | 8 weeks (RT) | 8 weeks (50° C.) |
| Concentration Ia-i (wt %) | 28.82 | 29.49 | 28.95 | 30.1 | 30.09 |
| Concentration imidacloprid (wt %) | 12.97 | 14.52 | 14.21 | 13.98 | 13.95 |
| Particle size (μm) | 1.95 | 1.917 | 1.961 | 1.813 | 1.832 |
| Viscosity (cP) | 49.68 | 61.6 | 68.1 | 52.19 | 61.92 |
| pH | 8.55 | 8.36 | 8.39 | 8.22 | 8.28 |

TABLE 23

Aged Stability Studies for Composition in Table 18

| | Time | | | | |
|---|---|---|---|---|---|
| | 0 | 4 weeks (RT) | 4 weeks (50° C.) | 8 weeks (RT) | 8 weeks (50° C.) |
| Concentration Ia-i (wt %) | 29.11 | 29.38 | 29.4 | 29.97 | 30.21 |
| Concentration imidacloprid (wt %) | 13.19 | 14.37 | 14.13 | 13.91 | 13.76 |
| Particle size (μm) | 1.939 | 1.867 | 1.924 | 1.817 | 1.883 |
| Viscosity (cP) | 77.03 | 86.7 | 104.39 | 82.64 | 101.28 |
| pH | 9.5 | 9.29 | 8.86 | 9.18 | 8.78 |

TABLE 24

Aged Stability Studies for Composition in Table 19

| | Time | | | | |
|---|---|---|---|---|---|
| | 0 | 4 weeks (RT) | 4 weeks (50° C.) | 8 weeks (RT) | 8 weeks (50° C.) |
| Concentration Ia-i (wt %) | 28.95 | 29.34 | 29.22 | 29.73 | 30.12 |
| Concentration imidacloprid (wt %) | 13.36 | 14.4 | 14.4 | 13.89 | 13.99 |
| Particle size (μm) | 1.916 | 1.902 | 1.885 | 1.859 | 1.864 |
| Viscosity (cP) | 61.23 | 63.54 | 70.48 | 56.8 | 64.73 |
| pH | 7.36 | 7.29 | 7.3 | 7.16 | 7.21 |

Example 25: Preparation of Suspension Concentrates Comprising 3-phenyl-5-(thiophen-2-yl)-1,2,4-oxadiazole (Ia-i)

Several suspension concentrate formulation compositions comprising the nematicidal compound 3-phenyl-5-(thiophen-2-yl)-1,2,4-oxadiazole (Ia-i) were prepared. A summary of three representative suspension concentrate formulation compositions prepared in this Example is provided below in Tables 25-27.

The phosphate buffer was prepared by adding potassium phosphate monobasic anhydrous (9.361 g) and sodium phosphate dibasic heptahydrate (32.732 g) to a 1 L volumetric flask. Then DI water was added to the flask to the mark. After it was shaken for a while, all the salts were dissolved to give a clear phosphate buffer with pH at 7.

The KELZAN thickener/stabilizer was prepared by adding KELZAN CC (4.00 g) and PROXEL GXL (8.00 g) to DI water (388.00 g) and agitating with a mechanical disperser at 2,900 rpm at room temperature for 30 minutes to obtain a viscous liquid (400 g). The same composition and preparation procedure were used to prepare KELZAN thickener/stabilizer with a scale up to 1 kg.

Ground Ia-i was prepared by adding it to a plastic bottle half filled with cylindrical ceramic beads (½" O.D.×½" long) and rotated for 30 minutes on a roller. Ground Ia-i was then collected after sieving through a screen and used in preparation of the suspension concentrate formulation.

The suspension concentrate formulation compositions were prepared by first preparing a formulation blank by adding MORWET D-425 (81.6 g) to DI water (1027.4 g) in a 1 gallon jar. After MORWET D-425 was dissolved, propylene glycol (204.1 g) phosphate buffer (34.0 g), PLURONIC L-35 (2.04 g), antifoam (11.34 g), and ISOPAR M (81.6 g) were added to the jar and it was then agitated in an ice bath with a homogenizer at 9,000 rpm for 6 minutes to give a brown emulsion (1442.1 g).

To a 1 gallon jar were added the formulation blank and ground Ia-i, and the resulting mixture was well stirred with a spatula. Then the jar was placed in an ice bath and a Tekmar homogenizer (model T 45 S4) was inserted into the slurry and the head of the homogenizer in the center of the jar was about 5 mm above the bottom of the jar. Initially it was operated at 10,000 rpm for 3 minutes and then at 9,000 rpm for 27 minutes. The particle size of the resulting slurry was measured after it was milled for 30 minutes. If large particles still existed in the formulation slurry, it was milled for additional 5 to 10 minutes. Particle size was measured by Beckman Coulter particle size analyzer (Beckman Coulter LS 13 320 laser diffraction particle size analyzer).

A NETZCH MINI ZETA II mill apparatus filled with glass beads with a diameter of 0.7-1 mm (200 ml) was used in the milling. The mill was connected to the water line and cold water was used to control the temperature increase during the milling. Before it was used, small amount of the formulation blank (15.0 g) was added to the machine first and the machine was then run at 3504 rpm for 30 s. Compressed nitrogen was used to push the residual formulation blank out of the machine.

For the preparation of the suspension concentrate formulations in this example, the pass method was used to reduce the particle size of the formulation. During the milling, the formulation slurry obtained from pre-milling as described above was added to the mill when operated at 3504 rpm. After milled through the mill, the formulation was collected. Then the same milling was repeated twice to give the formulation with an average median particle of about 2 μm with a particle size range of from about 1.6 to about 2.5 μm. If the particle size is still large, the fourth or additional milling is required.

In post treatment, the KELZAN thickener/stabilizer, humic acid sodium salt, and ATLOX 4913 were added to the collected formulation slurry and it was then stirred with a mechanical stirrer at room temperature for 30 minutes to obtain the suspension concentrate formulation in the form of a brown slurry. The wt % values reported in Tables 25-27 for the ATLOX 4913, stabilizer, humic acid sodium salt, and water are based on sample amounts recovered after milling (for example, if a total of 1000 g of formulation blank and nematicidal component are milled and 800 g are recovered after milling, the amount of post milling components added are based on 800 g).

TABLE 25

Formulation 7

| Ingredient | Wt % |
|---|---|
| MORWET D-425 | 2.17 |
| Buffer | 0.91 |
| Propylene glycol | 5.43 |
| ISOPAR M | 0.36 |
| Antifoam (1520-US) | 0.30 |
| PLURONIC L-35 | 0.05 |
| Ia-i | 45.88 |
| ATLOX 4913 | 4.00 |
| Stabilizer | 9.60 |
| Humic acid sodium salt | 2.17 |
| Water | 4.53 |

TABLE 26

Formulation 8

| Ingredient | Wt % |
|---|---|
| MORWET D-425 | 2.17 |
| Buffer | 0.91 |
| Propylene glycol | 5.43 |
| ISOPAR M | 2.17 |
| Antifoam (1520-US) | 0.30 |
| PLURONIC L-35 | 0.05 |
| Ia-i | 45.88 |
| ATLOX 4913 | 4.00 |
| Stabilizer | 9.60 |
| Humic acid sodium salt | 2.17 |
| Water | 27.32 |

TABLE 27

Formulation 9

| Ingredient | Wt % |
|---|---|
| MORWET D-425 | 2.17 |
| Buffer | 0.91 |
| Propylene glycol | 5.43 |
| ISOPAR M | 2.17 |
| Antifoam (BYK-016) | 0.30 |
| PLURONIC L-35 | 0.05 |
| Ia-i | 45.88 |
| ATLOX 4913 | 4.00 |
| Stabilizer | 9.60 |
| Humic acid sodium salt | 2.17 |
| Water | 27.32 |

Example 26: Preparation of Suspension Concentrates Comprising Nematicidal Compound and a Second Active Several suspension concentrate co-formulation compositions comprising the nematicidal compound 3-phenyl-5-(thiophen-2-yl)-1,2,4-oxadiazole (Ia-i) or 3-(4-chloro-2-methylphenyl)-5-(furan-2-yl)-1,2,4-oxadiazole (Ia-iii) and various fungicides or insecticides as a second active were prepared. A summary of sixteen representative co-formulation compositions (A-P) prepared in this Example is provided below in Tables 28-33.

The co-formulation compositions were prepared by adding DI water, MORWET D-425, phosphate buffer (as described above in Example 23) and propylene glycol to a 30 ml vial equipped with cap. After MORWET D-425 was dissolved, humic acid sodium salt, ISOPARM, antifoam (AGNIQUE DFM 111S), and PLURONIC L-35 were added to the vial and it formed a brown liquid after stirring. Then the actives were added to the vial according to the composition in each formulation. Stainless steel beads (14 ml) with a diameter of 2 mm were added to the vial and the vial was capped tightly. The vial was placed in a large jar (16 oz.) and the large jar was caped. The large jar with four vials were placed on a roller (model 764 AVM from U.S. Stoneware), and it was rolled at half of the maximum speed for 2 days at ambient temperature. KELZAN thickener/stabilizer (as described above in Example 23) was then added to the vial and rolled at 10-20% of the maximum speed for 4 hrs. The formulation, which was flowable in the vial, was collected and a small amount of the sample was taken for particle size analysis. The wt % values reported in Tables 28-33 are theoretical based on the weight of the active added. The purities of the metalaxyl, tebuconazole and kresoxim methyl actives used in this Example were 90%, 96.8% and 97.5%, respectively.

TABLE 28

Co-Formulation of Ia-i and Imidacloprid

| | A | | B | | C | |
|---|---|---|---|---|---|---|
| Ingredient | Amount (g) | Wt % | Amount (g) | Wt % | Amount (g) | Wt % |
| MORWET D-425 | 0.36 | 2.26 | 0.36 | 2.26 | 0.36 | 2.26 |
| Buffer | 0.15 | 0.94 | 0.15 | 0.94 | 0.15 | 0.94 |
| Propylene glycol | 0.90 | 5.66 | 0.90 | 5.66 | 0.90 | 5.66 |
| ISOPAR M | 0.36 | 2.26 | 0.36 | 2.26 | 0.36 | 2.26 |
| Antifoam | 0.05 | 0.31 | 0.05 | 0.31 | 0.05 | 0.31 |
| PLURONIC L-35 | 0.009 | 0.06 | 0.009 | 0.06 | 0.009 | 0.06 |
| Ia-i | 3.80 | 23.88 | 0.76 | 4.77 | 6.85 | 43.03 |
| Imidacloprid | 3.80 | 23.88 | 6.85 | 43.03 | 0.76 | 4.77 |
| Humic acid sodium salt | 0.36 | 2.26 | 0.36 | 2.26 | 0.36 | 2.26 |
| Stabilizer | 1.59 | 10.00 | 1.59 | 10.00 | 1.59 | 10.00 |
| Water | 4.53 | 28.47 | 4.53 | 28.47 | 4.53 | 28.47 |

TABLE 29

Co-Formulation of Ia-i and Tebuconazole

| | D | | E | | F | |
|---|---|---|---|---|---|---|
| Ingredient | Amount (g) | Wt % | Amount (g) | Wt % | Amount (g) | Wt % |
| MORWET D-425 | 0.36 | 2.26 | 0.36 | 2.26 | 0.36 | 2.26 |
| Buffer | 0.15 | 0.94 | 0.15 | 0.94 | 0.15 | 0.94 |
| Propylene glycol | 0.90 | 5.66 | 0.90 | 5.66 | 0.90 | 5.66 |
| ISOPAR M | 0.36 | 2.26 | 0.36 | 2.26 | 0.36 | 2.26 |
| Antifoam | 0.05 | 0.31 | 0.05 | 0.31 | 0.05 | 0.31 |
| PLURONIC L-35 | 0.009 | 0.06 | 0.009 | 0.06 | 0.009 | 0.06 |
| Ia-i | 3.80 | 23.88 | 0.76 | 4.77 | 6.85 | 43.03 |
| Tebuconazole | 3.80 | 23.88 | 6.85 | 43.03 | 0.76 | 4.77 |
| Humic acid sodium salt | 0.36 | 2.26 | 0.36 | 2.26 | 0.36 | 2.26 |
| Stabilizer | 1.59 | 10.00 | 1.59 | 10.00 | 1.59 | 10.00 |
| Water | 4.53 | 28.47 | 4.53 | 28.47 | 4.53 | 28.47 |

TABLE 30

Co-Formulation of Ia-i and kresoxim-methyl

| | G | | H | | I | |
|---|---|---|---|---|---|---|
| Ingredient | Amount (g) | Wt % | Amount (g) | Wt % | Amount (g) | Wt % |
| MORWET D-425 | 0.36 | 2.26 | 0.36 | 2.26 | 0.36 | 2.26 |
| Buffer | 0.15 | 0.94 | 0.15 | 0.94 | 0.15 | 0.94 |
| Propylene glycol | 0.90 | 5.66 | 0.90 | 5.66 | 0.90 | 5.66 |
| ISOPAR M | 0.36 | 2.26 | 0.36 | 2.26 | 0.36 | 2.26 |
| Antifoam | 0.05 | 0.31 | 0.05 | 0.31 | 0.05 | 0.31 |
| PLURONIC L-35 | 0.009 | 0.06 | 0.009 | 0.06 | 0.009 | 0.06 |
| Ia-i | 3.80 | 23.88 | 0.76 | 4.77 | 6.85 | 43.03 |
| kresoxim-methyl | 3.80 | 23.88 | 6.85 | 43.03 | 0.76 | 4.77 |
| Humic acid sodium salt | 0.36 | 2.26 | 0.36 | 2.26 | 0.36 | 2.26 |
| Stabilizer | 1.59 | 10.00 | 1.59 | 10.00 | 1.59 | 10.00 |
| Water | 4.53 | 28.47 | 4.53 | 28.47 | 4.53 | 28.47 |

TABLE 31

Co-Formulation of Ia-i and metalaxyl

| | J | | K | | L | |
|---|---|---|---|---|---|---|
| Ingredient | Amount (g) | Wt % | Amount (g) | Wt % | Amount (g) | Wt % |
| MORWET D-425 | 0.36 | 2.26 | 0.36 | 2.26 | 0.36 | 2.26 |
| Buffer | 0.15 | 0.94 | 0.15 | 0.94 | 0.15 | 0.94 |
| Propylene glycol | 0.90 | 5.66 | 0.90 | 5.66 | 0.90 | 5.66 |
| ISOPAR M | 0.36 | 2.26 | 0.36 | 2.26 | 0.36 | 2.26 |
| Antifoam | 0.05 | 0.31 | 0.05 | 0.31 | 0.05 | 0.31 |
| PLURONIC L-35 | 0.009 | 0.06 | 0.009 | 0.06 | 0.009 | 0.06 |

TABLE 31-continued

Co-Formulation of Ia-i and metalaxyl

| | J | | K | | L | |
|---|---|---|---|---|---|---|
| Ingredient | Amount (g) | Wt % | Amount (g) | Wt % | Amount (g) | Wt % |
| Ia-i | 3.80 | 23.88 | 0.76 | 4.77 | 6.85 | 43.03 |
| metalaxyl | 3.80 | 23.88 | 6.85 | 43.03 | 0.76 | 4.77 |
| Humic acid sodium salt | 0.36 | 2.26 | 0.36 | 2.26 | 0.36 | 2.26 |
| Stabilizer | 1.59 | 10.00 | 1.59 | 10.00 | 1.59 | 10.00 |
| Water | 4.53 | 28.47 | 4.53 | 28.47 | 4.53 | 28.47 |

TABLE 32

Co-Formulation of Ia-iii and imidacloprid

| | M | | N | | O | |
|---|---|---|---|---|---|---|
| Ingredient | Amount (g) | Wt % | Amount (g) | Wt % | Amount (g) | Wt % |
| MORWET D-425 | 0.36 | 2.26 | 0.36 | 2.26 | 0.36 | 2.26 |
| Buffer | 0.15 | 0.94 | 0.15 | 0.94 | 0.15 | 0.94 |
| Propylene glycol | 0.90 | 5.66 | 0.90 | 5.66 | 0.90 | 5.66 |
| ISOPAR M | 0.36 | 2.26 | 0.36 | 2.26 | 0.36 | 2.26 |
| Antifoam | 0.05 | 0.31 | 0.05 | 0.31 | 0.05 | 0.31 |
| PLURONIC L-35 | 0.009 | 0.06 | 0.009 | 0.06 | 0.009 | 0.06 |
| Ia-iii | 3.80 | 23.88 | 0.76 | 4.77 | 6.85 | 43.03 |
| imidacloprid | 3.80 | 23.88 | 6.85 | 43.03 | 0.76 | 4.77 |
| Humic acid sodium salt | 0.36 | 2.26 | 0.36 | 2.26 | 0.36 | 2.26 |
| Stabilizer | 1.59 | 10.00 | 1.59 | 10.00 | 1.59 | 10.00 |
| Water | 4.53 | 28.47 | 4.53 | 28.47 | 4.53 | 28.47 |

TABLE 33

Co-Formulation of Ia-i, imidacloprid, and metalaxyl

| | P | |
|---|---|---|
| Ingredient | Amount (g) | Wt % |
| MORWET D-425 | 0.36 | 2.26% |
| Propylene glycol | 0.90 | 5.65% |
| water | 4.53 | 28.46% |
| ISOPAR M | 0.36 | 2.26% |
| Humic Acid sodium salt | 0.36 | 2.26% |
| Ia-i | 2.54 | 15.93% |
| Imidacloprid | 2.54 | 15.93% |
| Metalaxyl | 2.54 | 15.93% |
| Antifoam | 0.05 | 0.31% |
| PLURONIC L-35 | 0.009 | 0.06% |
| Buffer Solution | 0.15 | 0.94% |
| Stabilizer | 1.59 | 9.99% |

A small amount of each sample of co-formulation compositions A-P was taken for particle size analysis. Particle size was measured by Beckman Coulter particle size analyzer (Beckman Coulter LS 13 320 laser diffraction particle size analyzer). The results are set forth below in Table 34.

TABLE 34

Particle Size for Co-Formulations

| Co-Formulation | Mean (µm) | Median (µm) | Mean/Median (µm) |
|---|---|---|---|
| A | 3.387 | 2.263 | 1.496 |
| B | 3.561 | 2.083 | 1.709 |
| C | 3.146 | 2.213 | 1.422 |
| D | 3.757 | 2.525 | 1.488 |
| E | 5.697 | 3.442 | 1.655 |
| F | 2.993 | 2.052 | 1.459 |
| G | 3.139 | 2.415 | 1.300 |
| H | 2.794 | 1.824 | 1.532 |
| I | 3.487 | 2.424 | 1.438 |
| J | 3.514 | 2.142 | 1.640 |
| K | 5.046 | 2.473 | 2.040 |
| L | 3.569 | 2.380 | 1.499 |
| M | 5.491 | 4.025 | 1.364 |
| N | 4.004 | 2.893 | 1.384 |
| O | 5.102 | 4.157 | 1.227 |
| P | 3.356 | 2.272 | 1.477 |

Example 27: Field Trial

In this Example, various nematicidal formulations were tested for nematicidal activity against soybean cyst nematode (SCN) in a soy microplot field trial. The tested formulations included ACCELERON F/I, a fungicide/insecticide seed treatment package available from Monsanto Company and containing pyraclostrobin, metalaxyl, fluxapyroxad and imidacloprid, both alone and in combination with a composition in accordance with the present invention containing the nematicidal compound 3-phenyl-5-(thiophen-2-yl)-1,2,4-oxadiazole (Ia-i), in particular Formulation 9 as described above in Table 27. Also tested was the combination of ACCLERON F/N, a fungicide+nematicide seed treatment package available from Monsanto Company and containing pyraclostrobin, metalaxyl, fluxapyroxad, clothianidin and *Bacillus firmus* with Formulation 9.

Microplots containing a Stough fine sandy loam soil were fumigated with methyl bromide. These plots were covered with a 114-p.m (4.5-mil) thick polyethylene tarp for 72 hours. The tarp was removed and plots were planted 45 days later. Four seeds were planted in each microplot. Treatments were arranged in a randomized complete block design with five replications. Microplots were watered with drip irrigation as needed. Maximum and minimum weekly temperatures and amount of rainfall were recorded for duration of the test.

A race 3 population of *Heterodera glycines* was increased on soybean (Coker 156) in a greenhouse. Light brown to tan colored cysts were dislodged from the roots with a strong water spray and collected on nested sieves with pore sizes of 850 and 250 I~m. Cysts were placed into 20-ml glass test tubes and crushed with a modified Seinhorst cyst crusher (21). The resultant suspension was passed through a 75-tx m-pore sieve nested on a 28-~m-pore sieve to remove broken cysts and debris. The inoculum was incorporated in the appropriate treatments by pipetting the nematode suspension into 10 depressions 5 cm deep and 2 cm wide within each microplot. Soil was then mixed with a garden hoe to a depth of 15 cm, obtaining an inoculum level of 2,000 eggs and J2/250 $cm^3$ soil.

Plant stand, height and plant vigor evaluations were made at 20 to 40 days after planting. The number of *Heterodera glycines* in each microplot was determined at soybean maturity. Six soil cores 2.25-cm-d×15-cm deep were collected from the soybean root zone in each microplot. *Heterodera glycines* cysts were extracted from 250 cm a soil by sieving as described for inoculum production. J2 passing through the sieves used to collect cysts were extracted from the suspension using gravity-screening. Final separation of J2 in the fraction collected on the 28-um pore sieve was by sucrose centrifugal flotation (sucrose specific gravity=1.13). Data was reported as the number of J2s, cysts, eggs, J2+ eggs. Additionally, the treatment reproductive factor (Rf) was provided; Rf=final population (Pf)/the initial population (Pi).

Table 35 summarizes the SCN Reproductive Factor for the tested formulations.

TABLE 35

| Treatment | | | SCN Reproductive Factor |
|---|---|---|---|
| Trt 1 | ACCELERON F/I | pyraclostrobin, metalaxyl, fluxapyroxad, imidacloprid | 138 |
| Trt 2 | ACCELERON F/I + Formulation 9 in Table 27 (0.25 mg/seed) | pyraclostrobin, metalaxyl, fluxapyroxad, imidacloprid + Formulation 9 (0.25 mg/seed) | 73 |
| Trt 3 | ACCELERON F/I + Formulation 9 in Table 27 (0.50 mg/seed) | pyraclostrobin, metalaxyl, fluxapyroxad, imidacloprid + Formulation 9 (0.50 mg/seed) | 34 |
| Trt 4 | ACCELERON F/N + Formulation 9 in Table 27 (0.50 mg/seed) | pyraclostrobin, metalaxyl, fluxapyroxad, clothianidin, Bacillus firmus + Formulation 9 (0.50 mg/seed) | 28 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and the associated drawings shall be interpreted as illustrative and not in a limiting sense.

What is claimed is:

1. A method of preparing a nematicidal aqueous suspension concentrate composition comprising an alkylaryl sulfonate dispersant, an organic solvent component comprising a paraffinic hydrocarbon solvent, and a dispersed solid particulate phase comprising a nematicidal component comprising a compound of Formula (I), Formula (II), or a salt thereof,

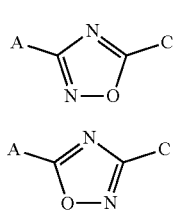

Formula I

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more substituents selected from the group consisting of F, Cl, $CH_3$, and $OCF_3$, the method comprising:

mixing the nematicidal component, the alkylaryl sulfonate dispersant, the organic solvent component, and water to form an aqueous suspension; and wet milling the aqueous suspension to produce a milled suspension having a reduced particle size, wherein the median size of solid particulates in the dispersed solid particulate phase of the milled suspension is less than about 10 μm.

2. The method of claim 1 wherein the median size of solid particulates in the dispersed solid particulate phase of the milled suspension is less than about 5 μm.

3. The method of claim 1 wherein the median size of solid particulates in the dispersed solid particulate phase of the milled suspension is from about 1 μm to about 5 μm.

4. The method of claim 1 wherein the mean particle size of solid particulates in the dispersed solid particulate phase of the milled suspension is less than about 20 μm.

5. The method of claim 1 wherein the mean particle size of solid particulates in the dispersed solid particulate phase of the milled suspension is from about 0.5 μm to about 10 μm.

6. The method of claim 1 wherein the milled suspension has a polydispersity index of less than about 10.

7. The method of claim 1 wherein the milled suspension has a polydispersity index of from about 1 to about 2.

8. The method of claim 1 wherein the wet milling step comprises ball milling.

9. The method of claim 1 wherein the nematicidal aqueous suspension concentrate composition further comprises a rheology modifying agent.

10. The method of claim 9 wherein the rheology modifying agent comprises a humic substance.

11. The method of claim 1 wherein a secondary dispersant is mixed with the nematicidal component, the dispersant, and water prior to the wet milling step.

12. The method of claim 1 wherein an antifreeze agent is mixed with the nematicidal component, the dispersant, and water prior to the wet milling step.

13. The method of claim 1 wherein a buffer solution is mixed with the nematicidal component, the dispersant, and water prior to the wet milling step.

14. The method of claim 13 wherein the pH of the aqueous suspension during the wet milling step is less than about 10.

15. The method of claim 1 wherein the milled suspension is combined with a stabilizer component.

16. The method of claim 1 wherein the milled suspension is combined with a one or more biological control agents.

17. The method of claim 1 wherein the nematicidal aqueous suspension concentrate composition further comprises an antifoam agent.

18. The method of claim 1 wherein the nematicidal component comprises a compound of Formula (I) or a salt thereof,

Formula I wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more substituents selected from the group consisting of F, Cl, $CH_3$, and $OCF_3$.

19. The method of claim 18 wherein the nematicidal component comprises a compound of Formula (Ia) or a salt thereof,

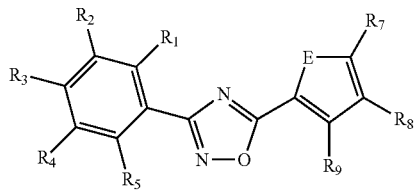

(Ia)

wherein $R_1$ and $R_5$ are independently selected from hydrogen, $CH_3$, F, Cl, Br, $CF_3$ and $OCF_3$; $R_2$ and $R_4$ are independently selected from hydrogen, F, Cl, Br, and $CF_3$; $R_3$ is selected from hydrogen, $CH_3$, $CF_3$, F, Cl, Br, $OCF_3$, $OCH_3$, CN, and C(H)O; $R_7$ and $R_8$ are independently selected from hydrogen and F; $R_9$ is selected from hydrogen, F, Cl, $CH_3$, and $OCF_3$; and E is O or S.

20. The method of claim 1 wherein the nematicidal component comprises a compound of Formula (II), or a salt thereof,

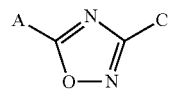

Formula II wherein A is selected from the group consisting of phenyl, pyridyl, pyrazyl, oxazolyl and isoxazolyl, each of which can be optionally independently substituted with one or more substituents selected from the group consisting of halogen, $CF_3$, $CH_3$, $OCF_3$, $OCH_3$, CN, and C(H)O; and C is selected from the group consisting of thienyl, furanyl, oxazolyl and isoxazolyl, each of which can be optionally independently substituted with one or more substituents selected from the group consisting of F, Cl, $CH_3$, and $OCF_3$.

* * * * *